(12) United States Patent
Noda

(10) Patent No.: US 10,161,793 B2
(45) Date of Patent: Dec. 25, 2018

(54) SPECTRUM ANALYSIS APPARATUS AND CALIBRATION METHOD

(71) Applicant: Shimadzu Corporation, Kyoto (JP)

(72) Inventor: Akira Noda, Nara (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 15/714,159

(22) Filed: Sep. 25, 2017

(65) Prior Publication Data

US 2018/0087961 A1   Mar. 29, 2018

(30) Foreign Application Priority Data

Sep. 26, 2016   (JP) .................... 2016-187457

(51) Int. Cl.
| | | |
|---|---|---|
| *G01J 3/00* | (2006.01) | |
| *G01J 3/02* | (2006.01) | |
| *G01N 21/27* | (2006.01) | |
| *G01N 30/74* | (2006.01) | |
| *G01J 3/10* | (2006.01) | |
| *G01J 3/18* | (2006.01) | |
| *G01N 21/25* | (2006.01) | |
| *G01J 3/42* | (2006.01) | |

(52) U.S. Cl.
CPC ............ *G01J 3/0262* (2013.01); *G01J 3/027* (2013.01); *G01J 3/10* (2013.01); *G01J 3/18* (2013.01); *G01J 3/42* (2013.01); *G01N 21/25* (2013.01); *G01N 21/274* (2013.01); *G01N 30/74* (2013.01)

(58) Field of Classification Search
CPC ........ G01J 3/02; G01J 3/18; G01J 3/10; G01J 3/42; G01N 21/25; G01N 21/27; G01N 30/74

See application file for complete search history.

(56) References Cited

U.S. PATENT DOCUMENTS

| 8,169,607 B2 | 5/2012 | Sano et al. |
| 9,086,316 B2 | 7/2015 | Gunji |
| 9,163,985 B2 | 10/2015 | Sano et al. |
| 2004/0195511 A1* | 10/2004 | Elmore .................. G01J 3/02 250/339.02 |

FOREIGN PATENT DOCUMENTS

| JP | H11-030552 A | 2/1999 |
| JP | 2010-117343 A | 5/2010 |
| JP | 2014-048232 A | 3/2014 |
| WO | 2013/145112 A1 | 10/2013 |

* cited by examiner

*Primary Examiner* — Abdullahi Nur
(74) *Attorney, Agent, or Firm* — Maier & Maier, PLLC

(57) ABSTRACT

In a spectrum analysis apparatus, a controller controls selection of an adequate the correction device based on a plurality of corrected absorption spectra corrected by a plurality of correction devices acquired in advance for eliminating an effect of stray light.

9 Claims, 9 Drawing Sheets

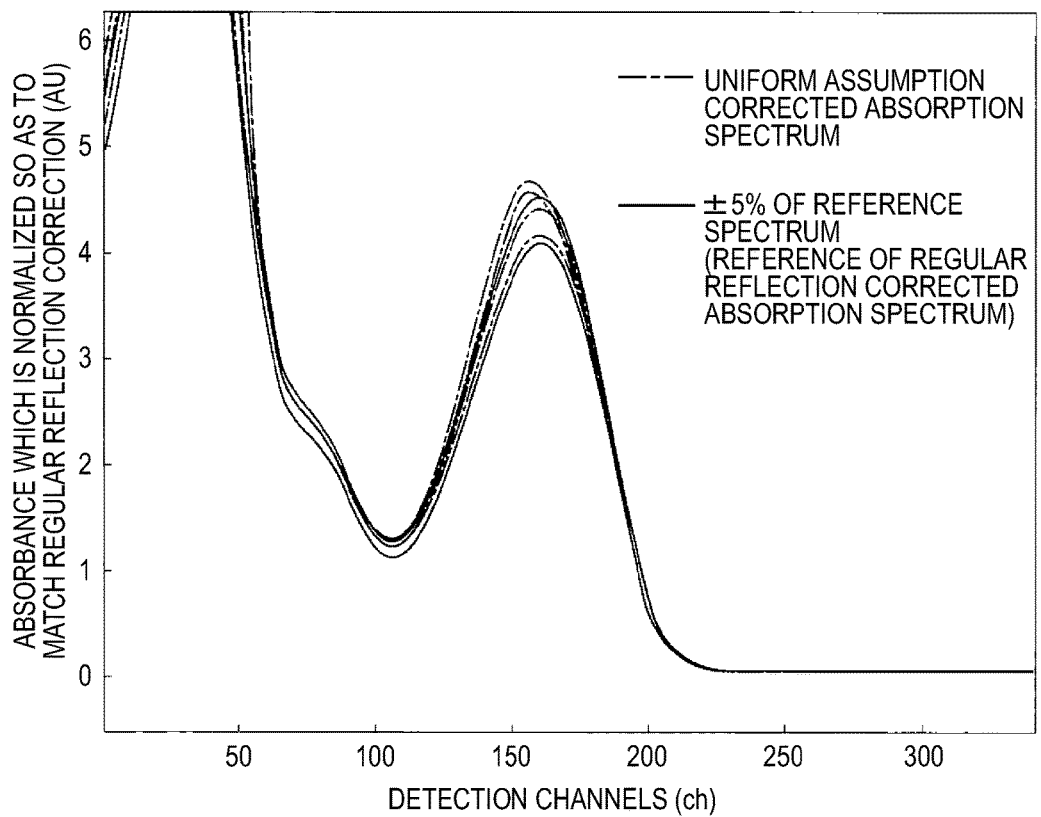

SPECTRUM ANALYSIS APPARATUS AND CALIBRATION METHOD

CROSS-REFERENCE TO RELATED APPLICATIONS

The priority application number JP2016-187457, SPECTRUM ANALYSIS APPARATUS AND CALIBRATION METHOD filed on Sep. 26, 2016, Akira Noda, upon which this patent application is based are hereby incorporated by reference.

BACKGROUND OF THE INVENTION

Field of the Invention

The present invention relates to a spectrum analysis apparatus and a calibration method capable of calibrating stray light.

Background Art

In the related art, spectrum analysis apparatuses capable of calibrating stray light are known. One of such spectrum analysis apparatuses is disclosed, for example, in JP-A-2014-48232.

JP-A-2014-48232 discloses an optical characteristic measurement apparatus (spectrum analysis apparatus) including a spectroscope, a detector configured to receive light split by the spectroscope, a detachable high-cut filter configured to cut wavelength components shorter than a predetermined wavelength from light incident on the spectroscope, and a processing unit configured to output results detected by the detector. The optical characteristic measurement apparatus disclosed in publication of JP-A-2014-48232 is configured to observe short wavelength components, which ideally should have been removed from light having passed through the high-cut filter and entering the spectroscope but actually have been detected therein by the detector to identify long wavelength components (stray light) incident on the detector from routes other than a normal route. The identified long wavelength components are then eliminated from the result of measurement, so that correction for eliminating an effect of stray light is achieved.

In addition, in the related art, a calibrating method in which monochromatic light rays associated with individual detection elements provided in a detector are sued as incident light to measure and acquire for each of the monochromatic light rays intensity ratios between incident light passing through a normal route and being observed by an intended detection element and stray light incident on and passing through abnormal routes and thus observed by a plurality of unintended detection elements.

However, with the optical characteristic measurement apparatus (spectrum analysis apparatus) in the JP-A-2014-48232 publication, although most part of the effect of the wavelength components passed through the high-cut filter on the wavelength components cut by the high-cut filter are eliminated, relationship between the wavelength components in the incident light and the wavelength components that appear as stray light cannot be figured out. Therefore, there remains a problem that the effect of stray light may not be eliminated accurately from a wavelength distribution in a result of measurement.

When the monochromatic light rays associated with the individual detection elements are used as incident light for calibration, measurement needs to be performed by the number of times of measurement corresponding to the total number of the detection elements. In addition, since the bandwidths of the monochromatic light rays are very narrow and thus a sufficient amount of light may not be obtained, measurement needs to be continued for a long time to obtain sufficiently accurate and reliable intensity ratios between the intensity of incident light passing through the normal route and incident on the intended detection elements and the intensity of the stray light passing through abnormal routes and incident on the intended detection elements. Consequently, the time required for measurement for calibration becomes disadvantageously huge. Accordingly, correction for eliminating the effect of stray light accurately from the wavelength distribution in a result of measurement in a short time is disadvantageously difficult.

In order to solve the above-described problems, it is an object of the invention to provide a spectrum analysis apparatus capable of performing correction for eliminating an effect of stray light accurately from a wavelength distribution in a result of measurement in a short time.

SUMMARY OF INVENTION

In order to achieve the above-described object, a spectrum analysis apparatus according to a first aspect of the invention includes: a spectral member configured to split light incident thereon by wavelength components; a detector configured to measure intensities of light rays split by the wavelength components by means of the spectral member; and a controller configured to perform calibration including a correction for eliminating an effect of stray light incident on the detector, which is light not to be measured, wherein the controller controls selection of an adequate correction device based on a plurality of corrected absorption spectra corrected by a plurality of the correction devices acquired in advance for eliminating the effect of stray light, the plurality of corrected absorption spectra being acquired by correcting a plurality of observed absorption spectra each indicating absorbance of light passing through a plurality of samples, the plurality of samples having the same light absorbing characteristic with varied degrees of light absorbance and having a peak increased in absorption coefficient for one or a plurality of wavelength components. As used in the invention the teen "the same light absorbing characteristic" is intended to include a characteristic that exhibits the same absorption coefficient (a constant determined depending on the type of a substance and indicating how much light the substance absorbs) for the same wavelength, which are established between the plurality of samples obtained by arbitrarily diluting the absorption concentration of the same samples.

As described above, the spectrum analysis apparatus according to the first aspect of the invention is provided with the controller that controls selection of an adequate correction device based on a plurality of corrected absorption spectra corrected by a plurality of the correction devices acquired in advance for eliminating the effect of stray light, the plurality of corrected absorption spectra being acquired by using each of a plurality of samples S by correcting the plurality of observed absorption spectra each indicating absorbance of light passing through the plurality of samples, the plurality of samples having the same light absorbing characteristic with varied degrees of light absorbance and having the peak increased in absorption coefficient for one or a plurality of wavelength components. Accordingly, a set of the plurality of corrected absorption spectra is acquired for a set of the plurality of observed absorption spectra having different degree of light absorbance individually by the plurality of correction devices, and the correction devices corresponding to the corrected absorption spectra with the effect of stray light eliminated adequately therefrom are selected from the set of the plurality of corrected absorption spectra. Therefore, correction for eliminating the effect of stray light accurately from the wavelength distribution in a result of measurement is achieved. In other words, the adequate correction devices may be selected based on the plurality of samples being different in degree of light absorption and having the same light absorbing characteristic. Once an adequate correction device specific for each instrument of the spectrum analysis apparatus is selected, spectra with the effect of stray light is eliminated therefrom may be acquired from then onward only by using the correction devices selected for the measured absorption spectra or fluorescent spectra in measurement of the samples. In addition, the adequate correction device may be selected only by performing measurement by the same number of times as the number of samples (for example, two to five samples), and calibration may be achieved by using the selected correction device. Therefore, time required for measurement may be significantly reduced compared with a case where stray light needs to be measured for each of a number of (for example, several hundreds to several thousands of) detection elements included in the detecting unit by using monochromatic light rays. In other words, by selecting an adequate correction device from the plurality of correction devices acquired in advance, calibration may be achieved in a short time. Consequently, correction for eliminating the effect of stray light accurately from the wavelength distribution in a result of measurement is achieved in a short time.

In the spectrum analysis apparatus according to the first aspect described above, preferably, the controller aligns the heights of the peaks of absorbance of the plurality of corrected absorption spectra at peak positions where the absorption coefficients become high for each of the correction devices, and based on the deviation of each of the plurality of corrected absorption spectra aligned in height from a reference spectrum, controls to select a correction device corresponding to the corrected absorption spectrum adequately corrected. In this configuration, based on a nature that the wavelengths of the plurality of corrected absorption spectra aligned in height match in an ideal condition having no effect of stray light, the corrected absorption spectra from which the effect of stray light has been adequately eliminated may be apparent from the margin of degree of deviation from the reference spectrum. Consequently, a correction device that corresponds to the corrected absorption spectrum from which the effect of stray light has been adequately eliminated and which is capable of eliminating the effect of stray light accurately from the wavelength distribution in a result of measurement may be selected. In addition, since the degree of deviation from the reference spectrum is acquired by aligning the height of the plurality of corrected absorption spectra, the heights (the peaks of absorption) of the corrected absorption spectra before alignment may be arbitrary. Accordingly, the heights of the observed absorption spectra which are the originals of the corrected absorption spectra may also be arbitrary. Therefore, accurate adjustment of the absorption concentrations of the plurality of samples having the same light absorbing characteristic is not necessary.

In this case, preferably, the controller controls selection of the correction device corresponding to the corrected absorption spectrum having a deviation within a predetermined range based on the deviation from the reference spectrum, which has a smallest sum of squares of the amounts of displacement from the plurality of corrected absorption spectra. In this configuration, the degree of deviation from the reference spectrum may be evaluated accurately, and thus whether or not the effect of stray light has been adequately eliminated may easily be determined. Consequently, the correction device that eliminates the effect of stray light accurately from the wavelength distribution in a result of measurement may be selected.

In the spectrum analysis apparatus of the first aspect described above, preferably, the correction device includes a stray light correction matrix, which is an inverse matrix of stray light matrix acquired in advance and indicating a correspondence relationship between the intensities of respective wavelengths of light incident on the detector and intensities appeared on the respective wavelength components as a result of detection. In this configuration, the corrected absorption spectrum on which the correction for eliminating the effect of stray light is applied may be acquired immediately from the observed absorption spectrum as a result of measurement by using an inverse matrix of the stray light matrix. Therefore, the correction for eliminating the effect of stray light accurately from the observed absorption spectrum in a result of measurement may easily be achieved.

In the spectrum analysis apparatus according to the first aspect described above, preferably, when the controller performs the calibration based on the plurality of observed absorption spectra acquired respectively by using the plurality of samples with varied degrees of light absorbance, the controller performs calibration based on the plurality of observed absorption spectra acquired respectively in the plurality of samples obtained by arbitrarily diluting the absorption concentration of the same samples. In this configuration, by varying the concentration of the same samples, calibration may be performed easily based on the plurality of samples having the same light absorbing characteristic with varied degrees of light absorbance. In addition, since the degree of dilution of the absorption concentration is arbitrary, accurate measurement is not necessary, and the plurality of samples may easily be prepared. As used in herein the term "dilute the absorption concentration" is to be considered, in a wide concept, intended to include not only a case of reducing the ratio of substance that absorbs light included in the sample, but also a case of reducing the length of a route of light passing through the sample to reduce the number of substances that absorb light included in an area in the sample where the light passes.

In the spectrum analysis apparatus according to the first aspect described above, preferably, the controller performs calibration for eliminating the effect of stray light regularly reflected by surface portions of the detection elements included in the detector and directed to the incident light or by a surface portion of a protective member of the detector mounted for protecting the detection elements. In this configuration, stray light having a regularity and being caused by regular reflection is also calibrated and thus the plurality of correction devices acquired in advance may easily matched an ideal correction device compared with the case of addressing the effect of irregular stray light generated by diffusion or irregular reflection. Accordingly, by selecting an adequate correction device from the plurality of correction devices acquired in advance, calibration may be achieved with high degree of accuracy.

In the spectrum analysis apparatus that performs calibration for removing the effect of regularly reflected stray light described above, preferably, the controller performs calibration when mounting at least one of the spectral member, the detector, or the protective member of the detector. In this configuration, even when the condition of occurrence of errors caused by regularly reflected stray light is changed when performing maintenance or replacement of the spectral member, the detector or the protective member of the detector, the effect of stray light may be eliminated adequately every time when performing calibration. Accordingly, erroneous measurement caused by stray light which is generated in a different manner by maintenance or replacement may be restrained.

In the spectrum analysis apparatus which performs calibration for eliminating the effect of regularly reflected stray light described above, preferably, the controller performs calibration based on the plurality of observed absorption spectra acquired from the sample having a peak of absorption coefficient in a relatively large wavelength band which is susceptible to a relatively large effect of regularly reflected stray light. In this configuration, the effect of stray light on the wavelength components especially around the peak may be accurately eliminated, and thus the effect of the regularly reflected stray light may be eliminated adequately by using the peak of the absorption coefficient existing in the relatively large wavelength band which is susceptible to a relatively significant effect of regularly reflected stray light.

A calibration method according to a second aspect of the invention is a calibration method including correction for eliminating an effect of stray light by a spectrum analysis apparatus including a spectral member configured to split light incident thereon by wavelength components and a detector configured to measure intensities of light rays split by the wavelength components by means of the spectral member, including: acquiring a plurality of observed absorption spectra each indicating absorbance of light passing through a plurality of samples by using each of the plurality of samples having the same light absorbing characteristic with varied degrees of light absorbance and having a peak increased in absorption coefficient for one or plurality of wavelength components, and selecting an adequate correction device based on a plurality of corrected absorption spectra corrected by a plurality of the correction devices acquired in advance for eliminating the effect of stray light.

As described above, the calibration method according to the second aspect of the invention includes the controller that controls selection of an adequate correction device based on a plurality of corrected absorption spectra corrected by a plurality of the correction devices acquired in advance for eliminating the effect of stray light, the plurality of corrected absorption spectra being acquired by correcting the plurality of observed absorption spectra each indicating absorbance of light passing through the plurality of samples, the plurality of samples having the same light absorbing characteristic with varied degrees of light absorbance and having the peak increased in absorption coefficient for one or a plurality of wavelength components. Accordingly, a set of the plurality of corrected absorption spectra is acquired for the individual correction devices for a set of observed absorption spectra having different degree of light absorbance by using the plurality of correction devices, and the correction device corresponding to the corrected absorption spectrum with the effect of stray light adequately eliminated is selected. Therefore, correction for eliminating the effect of stray light accurately from the wavelength distribution in a result of measurement is achieved. In other words, the adequate correction device may be selected based on the plurality of samples being different in degree of light absorption and having the same light absorbing characteristic. Once an adequate correction device specific for each instrument of the spectrum analysis apparatus is selected, spectra with the effect of stray light is adequately eliminated therefrom may be acquired from then onward only by using the correction devices selected for the measured absorption spectra or fluorescent spectra in measurement of the samples. In addition, the adequate correction device may be selected only by performing measurement by the same number of times as the number of samples (for example, two to five samples), and calibration may be achieved by using the selected correction device. Therefore, time required for measurement may be significantly reduced compared with a case where stray light needs to be measured for each of a number of (for example, several hundreds to several thousands of) detection elements included in the detecting unit by using monochromatic light rays. In other words, by selecting an adequate correction device from the plurality of correction devices acquired in advance, calibration may be achieved in a short time. Consequently, a calibration method capable of performing correction for eliminating the effect of stray light accurately from the wavelength distribution in a result of measurement in a short time is provided.

According to the invention, correction for eliminating the effect of stray light accurately from the wavelength distribution in a result of measurement in a short time is achieved as described above.

BRIEF DESCRIPTION OF DRAWINGS

FIG. 9 is a graph illustrating uniform assumption corrected absorption spectra for comparing with the regular reflection corrected absorption spectra having the substantially the same length according to a comparative example.

DETAILED DESCRIPTION OF INVENTION

Figure 1:
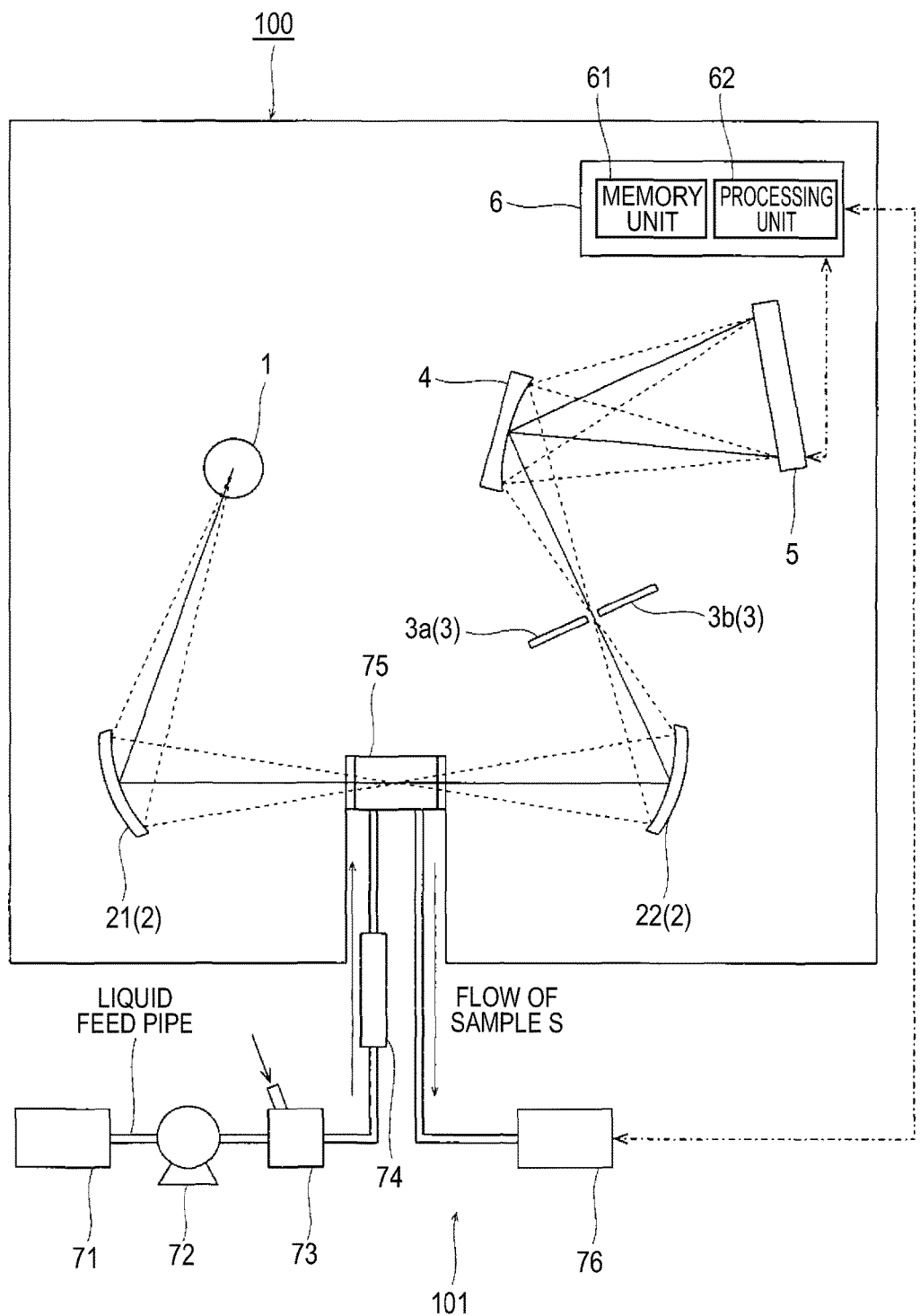
FIG. 1 is a block diagram illustrating a general configuration of a spectrum analysis apparatus according to an embodiment of the invention.

Referring now to the drawings, an embodiment in which the invention is embodied will be described.

Configuration of Spectrum Analysis Apparatus

Referring now to FIG. 1, a configuration of a spectrum analysis apparatus 100 according to the embodiment will be described. In this embodiment, an example in which a liquid chromatograph 101 is connected to the spectrum analysis apparatus 100 of the invention will be described.

As illustrated in FIG. 1, the spectrum analysis apparatus 100 is configured to make light incident on a sample S flowing in the liquid chromatograph 101 and measure wavelength components passed through the sample S, thereby acquiring light absorbance of the sample S for each of the wavelength components. The spectrum analysis apparatus 100 also includes a white light source 1, a reflecting portion 2, a shielding plate 3, a diffraction grating 4, a detector 5, and a controller 6. The diffraction grating 4 is an example of a spectral member in claims.

The white light source 1 is configured to irradiate the sample S with white light. The white light irradiated from the white light source 1 is configured to supply light having flat wavelength components stably in a wide wavelength band that covers the wavelength components to be measured. The white light source 1 includes, for example, tungsten lamps, xenon lamps, and deuterium discharge tubes.

The reflecting portion 2 includes a converging mirror 21 and a converging mirror 22. White light irradiated by the white light source 1 is reflected by a converging mirror 21 so as to be converged at a position of a flow cell 75, reaches the converging mirror 22, is reflected by the converging mirror 22 so as to be converged at a position of the shielding plate 3, and then is made incident on the diffraction grating 4. Note that the converging mirrors 21 and 22 are each formed of a concave mirror having an adequate curvature.

The shielding plate 3 is provided with a narrow slit interposed between plate portions 3a and 3b. The width of passage of the white light is reduced by being passed through the slit, so that light incident on the diffraction grating 4 may be aligned substantially in parallel. Accordingly, as the direction of the incident light is aligned, the incident light may be split by the wavelength components into light rays by interference of the diffraction grating 4.

The diffraction grating 4 is configured to reflect light incident thereon in different directions by interference depending on the wavelength components. Note that the diffraction grating 4 is formed, for example, of a grating mirror, which is a concave mirror, having grooves in a staircase pattern engraved regularly on a surface portion. In fact, zero-order light reflected in the same direction is generated irrespective of the wavelength components without causing any interference by the diffraction grating 4. However, the zero-order light poses little problem because it may be geometrically avoided by preventing the same from being directed to the detector 5 in the design phase. However, irregular stray light may be generated by zero-order light incident on the detector 5 as a result of diffused reflection or irregular reflection in the interior of the spectrum analysis apparatus 100. The zero-order light is reflected to a plurality of directions corresponding to a path difference between the incident light and reflected light by wavelengths also in the case of being reflected to a specific direction due to interference. Here, measurement is targeted at primary light having the highest diffraction efficiency and providing intense light. However, when high-order light from secondary light onward reflected in the directions different from the direction of reflection of the primary light is incident on the detector, such light is detected at positions different from the positions corresponding to the wavelength components, so that regular stray light may be caused. In addition, irregular stray light may be generated by high-order light incident on the detector 5 as a result of diffused reflection or irregular reflection in the interior of the spectrum analysis apparatus 100.

Figure 2A:
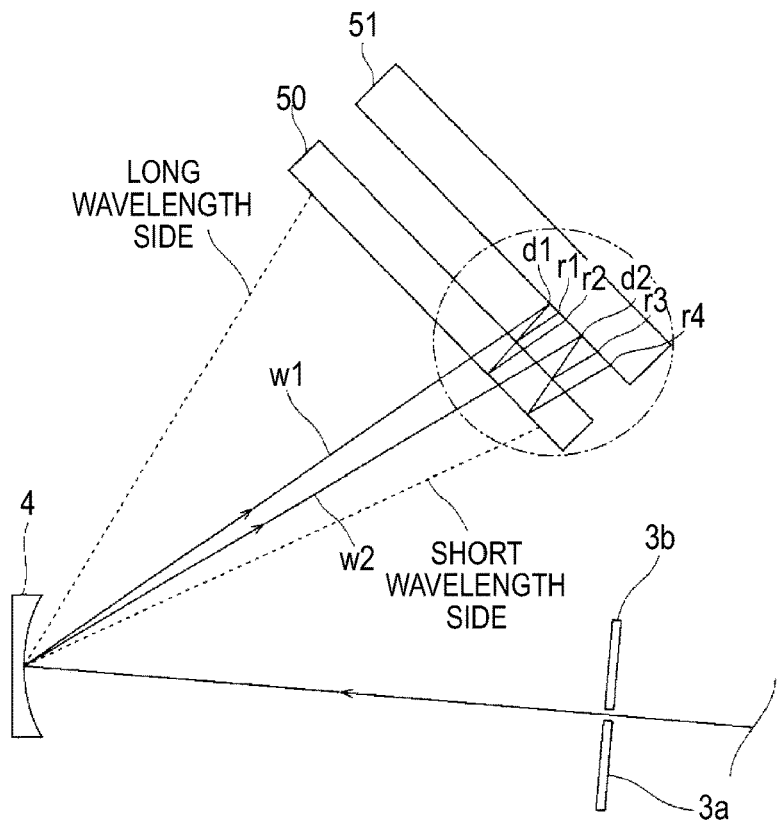
FIGS. 2A and 2B are schematic explanatory drawings illustrating stray light caused by regular reflection according to the embodiment of the invention.

The detector 5 includes a protective member 50 and a detecting unit 51 in the interior thereof as illustrated in FIG. 2A. The detecting unit 51 includes detection elements 52 that detects an intensity of light incident therein and transmits a signal (current) corresponding to the light intensity to the controller 6. The detection elements 52 are arranged at regular intervals in one-dimensional direction, and are each configured to transmit a detected spatial position of incident light to the controller 6 as a signal. A sufficient number (for example, several hundreds to several thousands) of the detection elements 52 are provided for measuring the intensity of light individually for the respective wavelength components. In other words, the incident positions of the respective wavelength components of the primary light reflected by the diffraction grating 4 into the detector 5 are determined geometrically in advance, and thus the wavelength components and the detecting positions may be correlated. The detector 5 is formed, for example, of a photodiode array having the detection elements 52 in a one-dimensional direction. In addition, the detecting unit 51 may be composed of a CCD (Charge Coupled Device) image sensor having the detection elements in a two-dimensional direction.

The controller 6 includes a memory unit 61 and a processing unit 62. The memory unit 61 is configured to acquire and memorize measurement data on intensities of light rays detected by the respective detection elements 52 corresponding to the wavelength components transmitted from the detector 5 together with measured time. The memory unit 61 memorizes various executable programs and data required for control including data on a stray light matrix $M_{(j)}$ and a stray light correction matrix $M^{-1}_{(j)}$ used for the correction of stray light. The processing unit 62 is configured to apply processing on acquired measurement data and acquire absorption spectra that indicate light absorbance of the sample S from measurement data on intensities of detected light rays. The data on the processed absorption spectra is memorized in the memory unit 61. The controller 6 is configured to acquire data on the intensities of detected light rays at real time at regular temporal intervals.

The liquid chromatograph 101 includes a mobile phase vessel 71, a pump 72, a sample injection part 73, a column 74, a flow cell 75, and a collection vessel 76, which are connected by a liquid feed pipe. A mobile phase (solvent) delivered from the mobile phase vessel 71 by the pump 72 carries a sample S injected from the sample injection part 73 to the column 74 for measurement. At this time, the transit velocity of each component contained in the sample S varies depending on an interaction with a stationary phase contained in the column 74, and thus the time period required for being transferred from the column to the flow cell 75 is specific for each component. Accordingly, in the flow cell 75, light absorbance of each component of the sample S may be measured individually. The sample S and the mobile phase measured in the flow cell 75 are collected in the collection vessel 76. Compositions of the mobile phase and the stationary phase, the thickness of the liquid feed pipe, and delivery flow rate of the pump 72 may be selected adequately depending on the type of the sample S to be measured. The controller 6 also serves as a drive controller for the liquid chromatograph 101 and also controls delivery of the mobile phase by the pump 72.

When measuring a sample S to be delivered by the liquid chromatograph 101, an absorption spectrum of the sample S which contains a plurality of substances mixed therein needs to be measured. Therefore, enhancement of linearity of an acquired signal (proportionality of an output signal with respect to an input signal) is desired. However, when stray light exists, wavelength components which are not essentially included in wavelengths of incident light are detected by the effect of the stray light. Therefore, stray light may cause overlooking of presence of substances contained in the sample S or erroneous recognition of the presence of substances which are not contained in the sample S when decomposing a measured absorption spectrum into absorption spectra of a plurality of substances. Therefore, in order to achieve an accurate measurement, adequate elimination of the effect of stray light is required.

Stray Light Correction

Figure 2B:
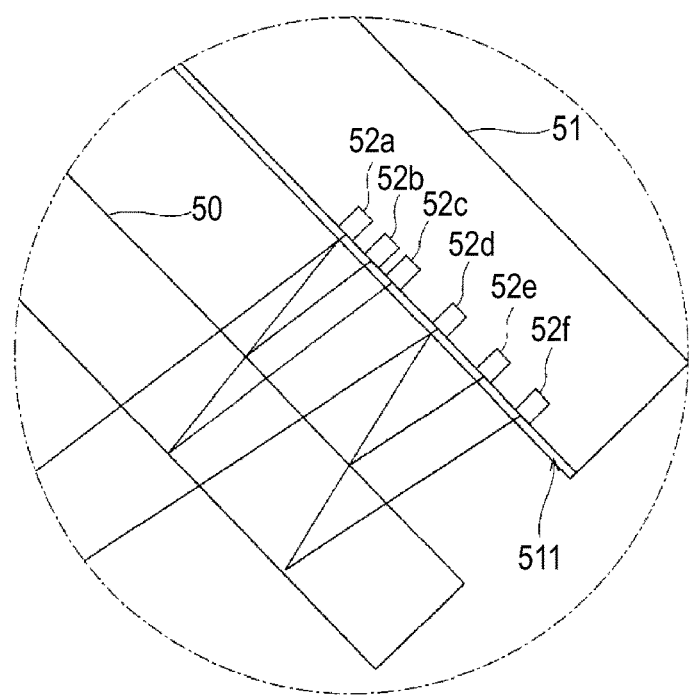
Figure 3:
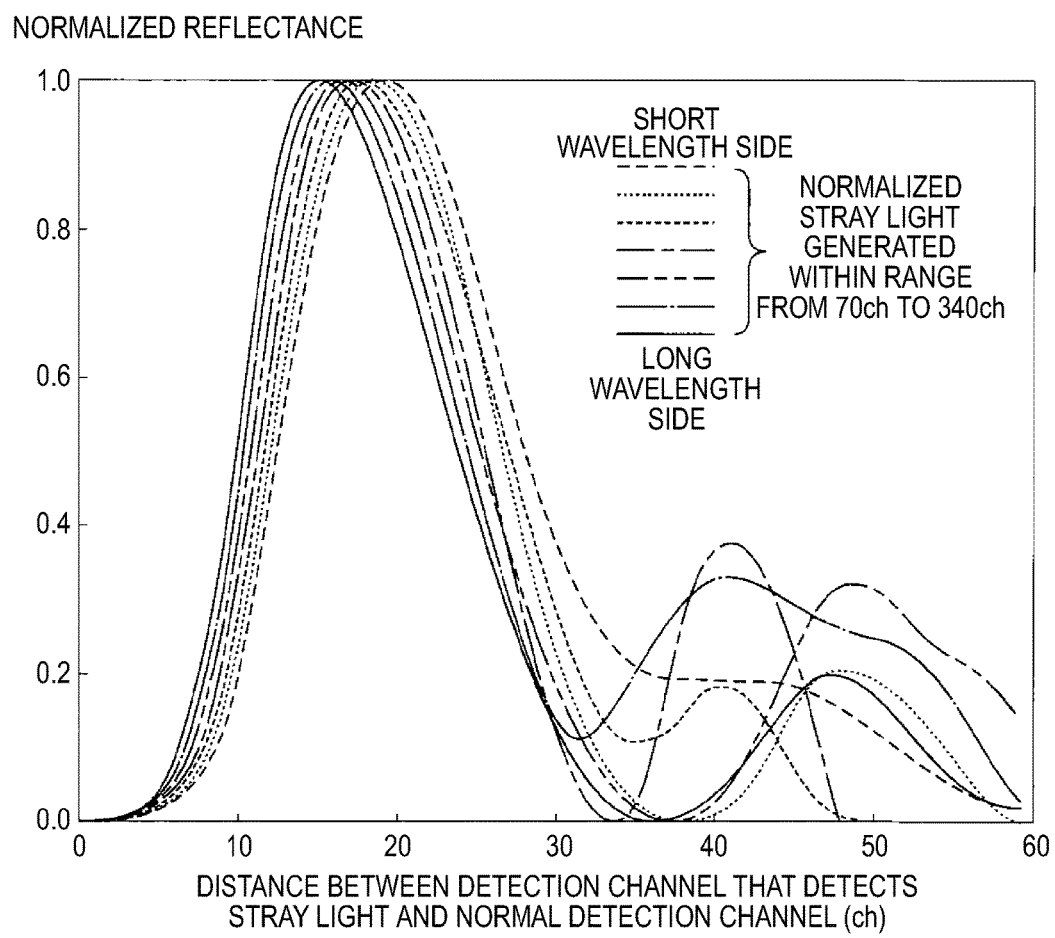
FIG. 3 is an explanatory graph illustrating an example of a stray light appearance distance caused by the regular reflection according to the embodiment of the invention.
Figure 4:
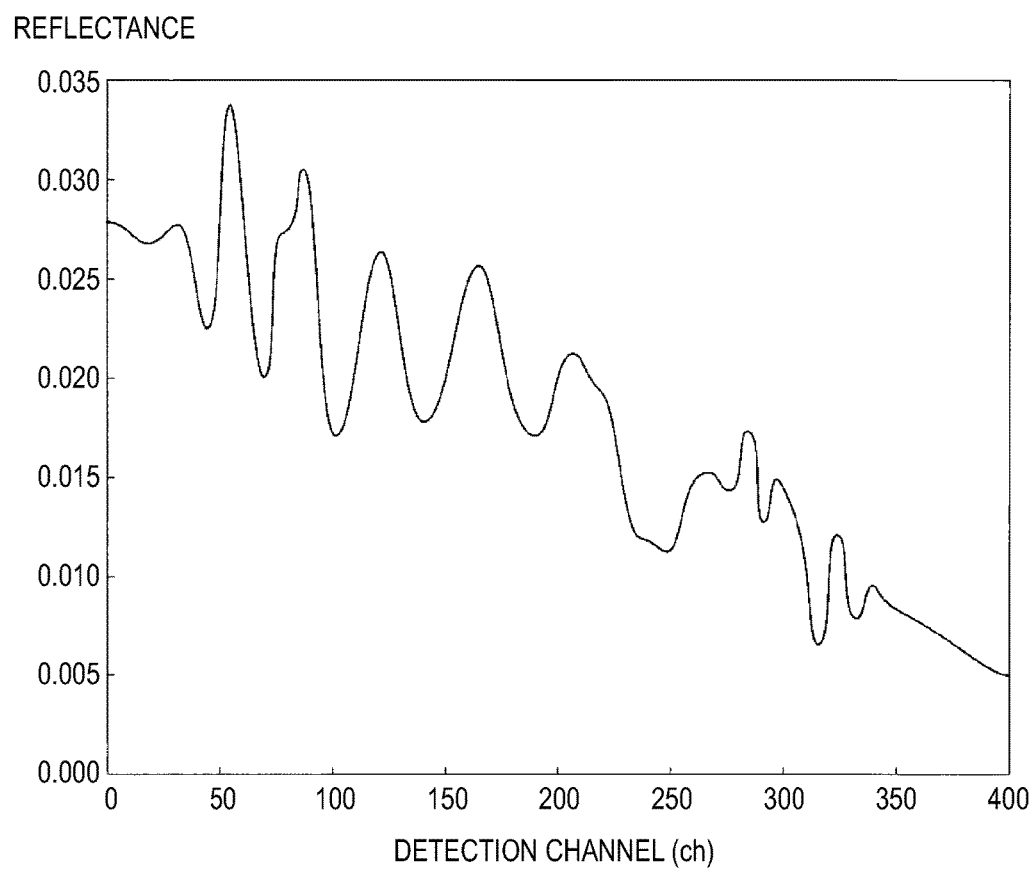
FIG. 4 is a graph illustrating an example of reflectance of stray light by wavelength caused by the regular reflection according to the embodiment of the invention.

Referring now to FIG. 2 to FIG. 4, correction for stray light is mainly focused in the calibration of the spectrum analysis apparatus 100 according to the embodiment below.

As illustrated in FIG. 2A, the detector 5 is provided with the protective member 50 at a portion directed to incident light, and the detecting unit 51 is protected by the protective member 50. In addition, as illustrated in FIG. 2B, which indicates an area surrounded by a dot-and-dash line in an enlarged scale in FIG. 2A, the detecting unit 51 includes detection elements 52a, 52b, 52c, 52d, 52e, and 52f in sequence covered with a silicon layer (SiO$_2$: silicon dioxide layer) 511 from a long wavelength side to a short wavelength side in the interior thereof. The detection elements 52a to 52f correspond to any one of N pieces of detection elements 52. The protective member 50 is formed of glass. The detecting unit 51 is a body portion of a photodiode array or a CCD image sensor. The protective member 50 and detecting unit 51 are fixed, for example, with an adhesive agent.

As illustrated in FIG. 2A, light passed through the slit portion of the shielding plate 3 is decomposed by wavelength components by means of the diffraction grating 4 and is reflected to directions corresponding to the respective wavelength components. At this time, reflected light beams of light incident on the diffraction grating 4 include long wavelength components on the side farther from the incident light, and short wavelength components on the nearer side from the incident light. Specifically, light w1 corresponds to a long wavelength component and light w2 corresponds to a short wavelength component. A range indicated by dot lines is a range of detectable wavelength components. Note that light reflected by the diffraction grating 4 illustrated in the drawing is light corresponding to primary light.

The light w1 incident on the detection elements 52 passes through the protective member 50, and then enters a position d1 of the detecting unit 51. At this time, components of light w1 which can enter the interior of the detecting unit 51 are detected by the detection elements 52 as detected light rays, and are converted into signals containing the positions of the corresponding detection elements 52 and intensities of the detected light rays, and then delivered to the controller 6. However, part of the components of the light w1 is subjected to regular reflection by the surface portion of the detecting unit 51, and then is subjected to regular reflection on the surface portion of the protective member 50 facing the detecting unit 51 or on the surface portion located on the opposite side from the detector 5, and these reflected light rays enter a position r1 or a position r2 of the detecting unit 51, respectively. In other words, the light w1, regularly reflected by the surface portions of the detecting unit 51 and the protective member 50, is partly detected at an erroneous position as stray light deviated from the normal route. Note that the positions d1, r1, and r2 corresponds to the detection elements 52a, 52b, and 52c, respectively.

As an example, approximately 25% of light (wavelength components) incident on the surface portion of the detecting unit 51 is reflected, and approximately 4% of light incident on the protective member 50 is reflected. Therefore, approximately 1% of light incident on and detected by the detection elements 52 together at normal positions is measured as stray light by the detection elements 52 at positions deviated from the original positions. Therefore, the normal measurement cannot be performed unless the effect of stray light is eliminated. In particular, if stray light enters the position corresponding to the wavelength components where essentially no light enter and light to be detected is substantially zero, the effect of detection of the stray light becomes disadvantageously significant. However, the ratios of the intensities of stray light generated by regular reflection are specific for the respective wavelength components due to interference in the interior of the silicon layer 511 of the detecting unit 51. Detailed description will be given later with reference to FIG. 4.

As illustrated in FIG. 2A, the light w2 entering the detection elements 52 is light having wavelength components shorter than those of the light w1. The light w2 also partly enters the interior of the detector 5 at the position d2 and is detected. However, part of the light w2 is regularly reflected from the surface portion of the detector 5. The reflected light w2 is regularly reflected by the protective member 50, enters a position r3 and a position r4, and is partly detected as stray light. In this case, as illustrated in FIG. 2B, the light w2 is detected by the detection elements 52d, 52e, and 52f.

A distance of the position r1 and the position r2 where stray light is detected from the normal detecting position d1 of the light w1 is different from a distance of the position r3 and the position r4 where stray light is detected from the normal detecting position d2 of the light w1. As such a difference is caused by the difference in incident angle, it may be calculated from the difference in geometric positional relationship. Specifically, a distance d1−r1 and a distance d2−r2 may be calculated from the incident angles of the light w1 and light w2 or a distance between the protective member 50 and the detecting unit 51. As apparent from FIG. 2B, the shorter the wavelength of light with respect to the light w1 is, the longer the distance between the normal detecting position and the detecting positions of stray light (hereinafter, referred to also as stray light appearance distance) becomes. Increase in the stray light appearance distance is substantially proportional to the distance between the normal detecting positions, and thus the stray light appearance distance may be calculated also for other wavelength components by acquiring the stray light appearance distance for some of the wavelength components.

FIG. 3 illustrates how far stray light may appear when the normal detecting position is normalized to a position of 0 ch. The vertical axis represents the reflectance of stray light, and is normalized so that so that the highest peaks are aligned to be 1. The lateral axis represents the channel numbers (ch) that correspond to respective detection elements 52. The larger the value of ch is, the longer wavelength can be detected. Specifically, FIG. 3 is a graph showing stray light appearing when the detection elements 52 are irradiated with impulses of a plurality of monochromatic light rays having corresponding wavelength components via the diffraction grating 4 with the light components detected at the normal positions eliminated and the heights aligned. The wavelength components that the monochromatic light rays have are selected as needed from a range corresponding to a range from 70 ch to 340 ch of the detection elements 52. It is understood from the graph that the peaks of the reflectance comes at more or less 20 ch. These peaks in FIG. 2A are stray light generated by the surface portion of the protective member 50 facing the detecting unit 51, which corresponds to the positions r1 and r3, and the largest stray light caused by regular reflection. As regards the peaks in reflectance at more or less 20 ch, those appeared on the side of larger channel number (right side) correspond more to monochromatic light rays having short wave lengths, and the stray light appearance distance varies depending on the wavelength. In FIG. 3, stray light appearing at channels larger than 30 ch is relatively small stray light such as stray light corresponding to the position r2 or r4 in FIG. 2A.

However, the surface portion of the protective member 50 and the surface portion of the detecting unit 51 may be considered to be substantially flat without irregularity or bending. However, both are not completely parallel to each other, and are placed at positions offset from the complete parallel within a range of geometric tolerance (an allowable range of error at the time of manufacture). Therefore, an increase in stray light appearance distance is specific for each instrument. In other words, calibration needs to be performed for each instrument. In this case, as described above, the stray light appearance distance may be calculated from the geometric proportional relationship. Therefore, in order to calibrate stray light generated in various positions depending on the geometric positional relationship between the surface portion of the protective member 50 and the surface portion of the detecting unit 51 and caused by regular reflection, the stray light appearance distance needs to be measured at least at two points; one on the short wavelength side and one on the long wavelength side.

Stray light caused by the high-order reflected light at the diffraction grating 4 may be treated in the same manner because the positions of occurrence of stray light are regularly determined depending on the positional relationship such as the distance and the angle among the diffraction grating 4, the protective member 50, and the detecting unit 51.

Referring now to FIG. 4, the reflectance of stray light will be described. The vertical axis of FIG. 4 represents the reflectance, which is a ratio of the intensity of stray light generated by regular reflection with respect to the intensity of light incident on the normal position. The lateral axis of FIG. 4 represents the channel corresponding to the detection element 52 number that detects the light. Here, For example, 0 ch corresponds to a wavelength component of approximately 190 nm, and 400 ch corresponds to a wavelength component of approximately 800 nm. As described above, the distance of the position where stray light is detected from the normal detecting position may be acquired from the geometric proportional relationship by measurement at least at two points. However, it is difficult to say how intense the stray light would be with respect to the intensity of light detected at the normal incident position. From the reflectance of the surface portion of the protective member 50 and of the surface portion of the detecting unit 51, it would be, for example, approximately 1%. In fact, however, the reflectance varies depending on the wavelength components because interference is caused by the silicon layer 511 provided on the surface of the protective member 50.

Therefore, as illustrated in FIG. 4, the reflectance generally tends to decrease substantially linearly with the detection channel number. However, the line has peaks and troughs which correspond to portions of constructive interference and portions of destructive interference depending on the wavelength components. The graph of the reflectance may be appeared in different shapes depending on the instruments due to the difference in thickness of the silicon layer 511 and a mounting angle with respect to the incident light. Specifically, shift to the left and the right of the wave shape of the graph (positions of peaks and troughs) may occur for each instruments corresponding to increase in reflectance as a whole corresponding to the constant addition, difference in inclination of the reflectance as a whole corresponding to the difference in rate of change, and difference in wavelength components where interference occurs.

In summary, the stray light appearance distance for other wavelength components may be calculated from the geometric arrangement by obtaining the stray light appearance distance at least at two points on the short wavelength side and the long wavelength side. In contrast, the reflectance of stray light is different depending on the wavelength. Therefore, in order to obtain the accurate reflectance, the intensity of light at the normal detecting position and the intensity of stray light need to be measured and compared for each of monochromatic light rays having the wavelength components corresponding to the respective detection elements 52. However, the difference in graph shape of the reflectance of stray light from one instrument to another also has regularity such as rising of the graph of the reflectance described above, change in inclination, and shift of the wave shape. Therefore, the shapes of the plurality of graphs acquired for the respective instruments change continuously, so that the tendency of the change in shape may be estimated to some extent.

Specifically, accurate samples of the stray light appearance distance or the reflectance of the stray light are obtained by making the monochromatic light rays incident on each of the detection elements 52 for a number of instruments in advance and measuring for the entire wavelength band. Accordingly, how the detected light including stray light appears with respect to the incident light may be expressed as Expression (1) given below, $$\text{Out} = M \cdot \text{In} \tag{1}$$

In Expression (1), In is a spectrum of light incident on the spectrum analysis apparatus 100, and Out is a spectrum of light actually detected by the spectrum analysis apparatus 100. The spectrum is a set of values that indicate the intensities of the wavelength components corresponding to the respective detection elements 52. M is a stray light matrix and is obtained by repeating measurement for detecting the detection spectrum Out with the incident spectrum In assuming a monochromatic light ray. The detection spectrum Out and the stray light matrix M are specific for each instrument in the spectrum analysis apparatus 100.

If the stray light matrix M is acquired, the incident spectrum In may be calculated easily from the detection spectrum Out, which is an actual measured value, by using a stray light correction matrix $M^{-1}$, which is an inverse matrix of the stray light matrix M as Expression (2) given below. The stray light correction matrix $M^{-1}$ is an example of a "correction device" in Claims.

$$\text{In} = M^{-1} \cdot \text{Out} \tag{2}$$

The stray light matrix M correlates the incident spectrum In to all the detection spectra Out that contain not only regular stray light caused by regular reflection but also irregular stray light (stray light which may be approximated to be uniform) generated by high-order reflected light, irregular reflection or diffused reflection. In other words, the effect not only of stray light caused by regular reflection, but also of all the stray light may be eliminated at once. The stray light having regularity generated by regular reflection appears in the vicinity of the normal detecting position, and thus has a value only in the vicinity of diagonal component of the stray light matrix M, and is zero-value at other portions. Also, irregular stray light caused by irregular reflection and diffused reflection may be separated with all the components being a constant value. Therefore, the stray light matrix M may be separated into the matrix having the components only in the vicinity of the diagonal component and a constant matrix, and thus the amount of calculation for calculating the stray light correction matrix $M^{-1}$ which is an inverse matrix from the stray light matrix M is reduced and the calculation time may be reduced. Calculation that uses the stray light matrix M and the stray light correction matrix $M^{-1}$ in spectra may also be finished in a short time.

As described above, if the stray light matrix M is acquired in advance by measuring which intensity of the spectra of the detection light may appear in which detection elements 52 when making monochromatic light rays having wavelength components corresponding to the respective detection elements 52 and having a certain intensity incident, the incident spectrum In may be calculated from a given detection spectrum Out. Except for a change in sensitivity due to deterioration of the detection elements 52 and replacement of parts relating to the optical route for maintenance, once such calibration is performed, accurate spectra of incident light may be calculated from then onward any time from the spectra of the detected light in measurement.

Therefore, individual stray light matrixes $M_{(j)}$ are acquired for a number of instruments (for example, 100 instruments) in advance, and then an adequate stray light matrix $M_{(j)}$ is selected at the time of calibration. Reference sign j is a number corresponding to the instrument and simulation. The way that stray light is generated by regular reflection has regularity, and thus the stray light matrixes $M_{(j)}$ corresponding to the state of generation of stray light near by maybe interpolated. For example, an interpolative stray light matrix $M_{(j)}$ that makes the state of generation of stray light change continuously may be created between the two stray light matrixes $M_{(j)}$ which are slightly deviated in state of generation of stray light by simulation. In other words, by listing characteristics of the state of generation of stray light that may exist within a range of geometric tolerance such as the mounting angle between the protective member 50 and the detecting unit 51 and the thickness of silicon on the detecting unit 51, data of the interpolative stray light matrixes $M_{(j)}$ created by simulation is stored in the memory unit 61. Therefore, the stray light matrixes $M_{(j)}$ by the number more than the number of instruments to be measured actually is acquired. Since the components generated by irregular stray light are treated as being uniformly generated, they are treated as constant values which do not change depending on the detection elements 52, for example, in the simulation.

In this embodiment, the controller 6 controls selection of an adequate stray light correction matrix $M^{-1}_{(j)}$ based on a plurality of corrected absorption spectra $Sc_{(j)}$. The plurality of corrected absorption spectra $Sc_{(j)}$ are acquired by correcting a plurality of observed absorption spectra So each indicating absorbance of light passing through a plurality of samples S by a plurality of stray right correction matrix $M^{-1}_{(j)}$ acquired in advance for eliminating the effect of stray light. The plurality of observed absorption spectra So are obtained by using the plurality of samples having the same light absorbing characteristic with varied degrees of light absorbance and having a peak increased in absorption coefficient for one or plurality of wavelength components.

In this embodiment, the controller 6 aligns the heights of the peaks of absorbance of the plurality of corrected absorption spectra $Sc_{(j)}$ at peak positions where the absorption coefficient becomes high for each of the stray light correction matrixes $M^{-1}_{(j)}$ and based on the degree of deviation of each of the plurality of corrected absorption spectra $Sc_{(j)}$ aligned in height from a reference spectrum $Sr_{(j)}$, controls the selection of the stray light correction matrix $M^{-1}_{(j)}$ corresponding to the corrected absorption spectrum $Sc_{(j)}$ adequately corrected.

In this embodiment, when performing the calibration based on the plurality of observed absorption spectra So acquired respectively by using the respective samples S with varied degrees of light absorbance, the controller 6 performs calibration based on the plurality of observed absorption spectra So acquired respectively in the plurality of samples S obtained by arbitrarily diluting the absorption concentration of the same samples S.

Specifically, the controller 6 acquires light intensity spectra that have transmitted through the samples S and also acquires observed absorption spectra So that indicate absorbances of the samples S by the wavelength components based on the acquired transmitted light spectra and the light intensity spectra irradiated from the known white light source 1. The controller 6 also acquires the plurality of observed absorption spectra So for each of light transmitted through the plurality of samples S having different absorption concentrations. The absorbance is a value obtained by taking logarithms of a ratio between the intensity of light before passing through the sample S (light irradiated from the white light source 1) and the intensity of light after having passed through the sample S (observed absorption spectrum So) for each of the wavelength components.

The sample S which may be used here is, for example, a caffeine solution. By diluting the concentration of the caffeine contained in the sample S with pure water, the light absorption concentration of the sample S is reduced while maintaining the same light absorbing characteristic. The plurality of samples S include those having relatively high absorption concentrations, which absorb light having wavelength components at positions of peaks of absorption substantially completely and those having relatively low absorption concentrations that are diluted arbitrarily by pure water. The plurality of, for example, five types of samples S having absorption concentrations different from each other are prepared. Note that even though foreign substances (contamination) are generated in caffeine contained in the samples S, it is not necessary to prepare completely pure caffeine because the caffeine exhibits the same light absorbing characteristic including absorption by foreign substances by diluting the samples S with pure water. In addition, the spectra of the sample S may be of any shape as long as steep peaks having sufficiently high absorbances and substantially narrow width are obtained, and do not have to have the same wave shape obtained from pure caffeine. If the observed absorption spectra having different amounts of light absorbance are obtained, calibration is enabled, so that the caffeine solution may have any concentration. In other words, although it is difficult to prepare a completely pure caffeine solution having an accurate concentration (for example, an accurate mass molarity), completely preventing contamination by impurities or performing precise concentration adjustment are not required, and thus preparation of the plurality of samples S configured as described above is easy.

Subsequently, the processing unit 62 acquires a set of corrected absorption spectra $Sc_{(j)}$ by using the stray light correction matrixes $M^{-1}_{(j)}$ acquired in advance for the set of observed absorption spectra So. As used herein the term "set" is intended to include a group of a plurality of observed absorption spectra So obtained by a plurality of samples S. The set of the corrected absorption spectra $Sc_{(j)}$ is a group of the corrected absorption spectra $Sc_{(j)}$ obtained as a result of using the same stray light correction matrix $M^{-1}_{(j)}$ for the set of the observed absorption spectra So. The stray light matrixes $M_{(j)}$ include those based on instrument having a state of generation of stray light similar to those of the spectrum analysis apparatus 100 to be calibrated, and also those based on instruments having completely different state of generation of stray light. As sufficiently various stray light matrixes $M_{(j)}$ are acquired in advance, the stray light matrixes $M_{(j)}$ include a stray light matrix $M_{(j)}$ based on an instrument having substantially the same state of generation of stray light as the instrument to be calibrated. Therefore, calibration with high degree of accuracy is achieved by selecting an adequate stray light matrix $M_{(j)}$.

In order to select an adequate stray light correction matrix $M^{-1}_{(j)}$, the set of the corrected absorption spectra $Sc_{(j)}$ obtained as a result of correction may be inspected. The respective corrected absorption spectra $Sc_{(j)}$ which are included in a certain set are obtained by performing correction for eliminating the assumed effect of stray light for the set of observed absorption spectra So that transmit through the samples S having the same light absorbing characteristic and different concentrations from each other. Therefore, although the respective corrected absorption spectra $Sc_{(j)}$ are different in amount of light absorbed during transmission, if stray light has been adequately eliminated, the fact that the light absorbance has been effected at the completely same position should be reflected.

In other words, if the heights of the peaks of absorption of the plurality of corrected absorption spectra $Sc_{(j)}$ obtained by using the same stray light correction matrix $M^{-1}_{(j)}$ are aligned to the corrected absorption spectrum $Sc_{(j)}$ having the highest peak by performing constant multiplication on the respective corrected absorption spectra $Sc_{(j)}$ entirely, for example, the corrected absorption spectra $Sc_{(j)}$ should completely match each other as a whole. In contrast, if the effect of stray light is not adequately eliminated, the corrected absorption spectra $Sc_{(j)}$ do not match each other as a whole due to the effect of stray light even though the heights at the peak positions are aligned. In other words, by comparing the sets of the corrected absorption spectra $Sc_{(j)}$ aligned in height at the peak positions and obtained by using the same stray light correction matrix $M^{-1}$, an adequate stray light correction matrix $M^{-1}$ is found.

Here, in this embodiment, the controller 6 aligns the heights of the peaks of absorbance of the plurality of corrected absorption spectra $Sc_{(j)}$ at the peak positions where the absorption coefficient becomes high for each of the stray light correction matrixes $M^{-1}$, and based on the deviation of each of the plurality of corrected absorption spectra $Sc_{(j)}$ aligned in height from a reference spectrum $Sr_{(j)}$, controls the selection of the stray light correction matrix $M^{-1}_{(j)}$ corresponding to the corrected absorption spectrum $Sc_{(j)}$ adequately corrected.

Specifically, the controller 6 calculates a reference spectrum $Sr_{(j)}$ that has the minimized sum of squares of the amount of displacement with respect to each of the corrected absorption spectra $Sc_{(j)}$ in a certain set to acquire square errors (sums of squares of the amount of displacement) $\delta_{(j)}$ between the reference spectrum $Sr_{(j)}$ and the corrected absorption spectra $Sc_{(j)}$. The stray light correction matrix $M^{-1}_{(j)}$ corresponding to j, which provides the minimum square error $\delta_{(j)}$ provides a corrected absorption spectrum $Sc_{(j)}$ having the highest coincidence when the heights are aligned. Accordingly, the controller 6 is capable of selecting the stray light correction matrix $M^{-1}_{(j)}$ which is an adequate correction device.

The selection of the stray light correction matrix $M^{-1}_{(j)}$ may be performed by a round robin method. However, for time saving, for example, an adequate stray light correction matrix $M^{-1}_{(j)}$ is searched along a tree diagram of the stray light correction matrixes $M^{-1}_{(j)}$ divided into groups sorted by similarity of tendency. Data of the stray light correction matrix $M^{-1}_{(j)}$ is divided into several groups sorted by similarity of tendency. A representative stray light correction matrix $M^{-1}_{(j)}$ is determined for each group. The processing unit 62 uses the representative stray light correction matrixes $M^{-1}_{(j)}$ of the groups for the observed absorption spectra So by the round robin method, and selects a group to which the stray light correction matrix $M^{-1}_{(j)}$ having the smallest square error belongs to. Each group is divided into subgroups of stray light correction matrixes $M^{-1}_{(j)}$ having similar tendencies, and in the same manner as described above, an adequate subgroup is selected by performing the round robin method to the respective representative stray light correction matrixes $M^{-1}_{(j)}$ in the subgroups within the selected group. The respective subgroups are also divided into sub subgroups, and are grouped as the tree diagram in which large groups are respectively branched into smaller groups. After the smallest set of the smallest stray light correction matrixes $M^{-1}_{(j)}$ is selected, an adequate stray light correction matrix $M^{-1}_{(j)}$ is selected from the smallest set.

Here, in this embodiment, the controller 6 performs calibration for eliminating the effect of stray light regularly reflected by a surface portion directed to the incident light of the detection elements 52 included in the detector 5 or a surface portion of the protective member 50 of the detector 5 mounted for protecting the detection elements 52.

Specifically, the stray light correction matrix $M^{-1}_{(j)}$ includes, as described above, portions corresponding to irregular stray light caused by diffused reflection, irregular reflection, and scattered light and portions corresponding to the regular stray light caused by regular reflection. The portion corresponding to the irregular stray light may be considered to be substantially constant matrix from their uniformity, and thus an effect of deriving $M^{-1}_{(j)}$ which may be theoretically estimated by simulation is hardly achieved. Accordingly, by including the stray light caused by regular reflection which significantly depends on the difference of instrument, the effect of deriving the $M^{-1}_{(j)}$ which may be theoretically estimated by simulation can easily appear.

In this embodiment, the controller 6 performs calibration when mounting at least one of the diffraction grating 4, the detector 5, or the protective member 50 of the detector 5.

Specifically, calibration of the spectrum analysis apparatus 100 is performed before shipment, and is also performed when replacing or mounting the diffraction grating 4, the detector 5, and the protective member 50 of the detector 5 after maintenance. As the position of generation of stray light due to regular reflection varies depending on the geometric mounting position of the diffraction grating 4, the detector 5, or the protective member 50 of the detector 5 and on variations due to individual differences, calibration is required. In particular, as the detector 5 has a limited lifetime, replacement is required. However, since the thickness of the silicon layer 511 on the detector 5 or the geometric position of the protective member 50 changes, calibration is inevitable. The same applies when the detector 5 is dismounted for cleaning.

In this embodiment, the controller 6 performs calibration based on the plurality of observed absorption spectra $So_{(j)}$ acquired from the samples S having peaks of absorption coefficient in a relatively large wavelength band which is susceptible to a relatively significant effect of the regularly reflected stray light.

Specifically, the magnitude of reflectance of stray light caused by regular reflection varies, for example, with the wavelength of light to be detected (the detection elements 52) as illustrated in FIG. 4. Therefore, the accuracy is enhanced by performing calibration by using the sample S having a peak at a wavelength at which the reflectance is particularly high. The graph of the reflectance in FIG. 4 is an example only, and a configuration in which the reflectance is high on a side of larger channel number and low on a side of smaller channel number depending on the mounting position of the detector 5 with respect to the diffraction grating 4. The reflectance may be changed depending on the type of the substance to be measured.

By using the stray light correction matrix $M^{-1}_{(j)}$ which is an adequate correction device selected in the manner described above, stray light specific for each spectrum analysis apparatus 100 may be eliminated adequately in measurement of samples S from then onward. Specifically, spectra from which the effect of stray light is adequately eliminated may be acquired by using the selected correction devices for absorption spectra or fluorescent spectra acquired from the sample S in the measurement of the samples from then onward.

Stray Light Matrix Preparation Process

Figure 5:
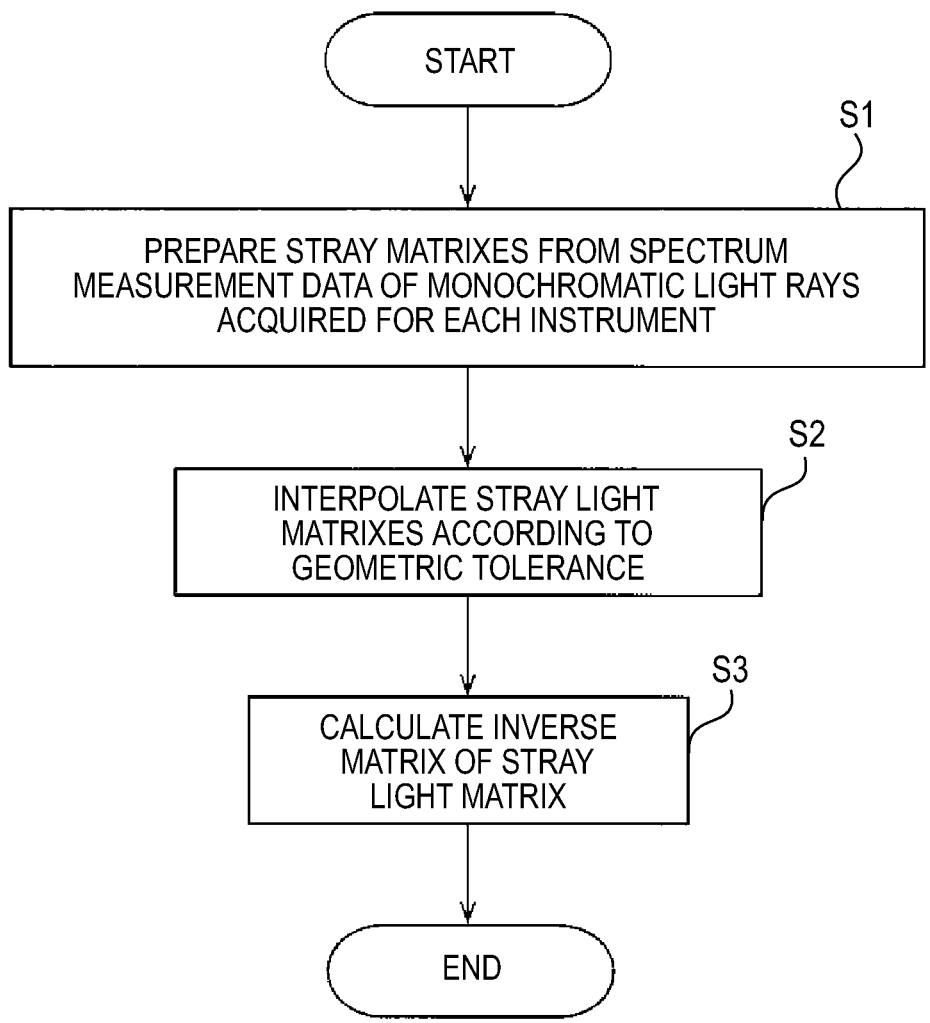
FIG. 5 is a flowchart illustrating a process of preparing a stray light correction matrix preparation process according to the embodiment of the invention.

Referring now to FIG. 5, a stray light matrix preparation process will be described below by using a flowchart. The stray light matrix preparation process is a process of acquiring a stray light matrix $M_{(j)}$ from data of a number of spectra measured by using monochromatic light rays for each instrument, and further creating a stray light matrix $M_{(j)}$ from the acquired stray light matrix $M_{(j)}$ by simulation. Note that the stray light matrix preparation process may be performed for each spectrum analysis apparatus 100, or may be performed by storing result data of obtained from outside in the memory unit 61 of the spectrum analysis apparatus 100.

When the stray light matrix preparation process is started, in Step S1, the processing unit 62 calculates a number of stray light matrixes $M_{(j)}$ corresponding to the respective instruments based on data on detected spectra including incident spectra and stray light of monochromatic light rays acquired for the respective instruments of a number of the spectrum analysis apparatuses 100 from the memory unit 61 or from the outside, and then the procedure goes to Step S2.

In Step S2, the processing unit 62 changes the geometric positional relationship between the protective member 50 and the detecting unit 51 or the thickness of the silicon layer 511 within a range of the geometric tolerance based on simulation to prepare stray light matrixes $M_{(j)}$ interpolated by changing the plurality of stray light matrixes $M_{(j)}$ calculated from the measurement data of spectra of monochromatic light rays. When a specified number of the stray light matrixes $M_{(j)}$ are acquired, the procedure goes to Step S3.

In Step S3, the processing unit 62 calculates the stray light correction matrixes $M^{-1}_{(j)}$ which are inverse matrixes of the stray light matrixes $M_{(j)}$ obtained by being prepared by measurement with monochromatic light rays and simulation, sends and memorizes the results of data into the memory unit 61, whereby the stray light correction matrix preparation process is ended.

Stray Light Correction Matrix Selection Process

Figure 6:
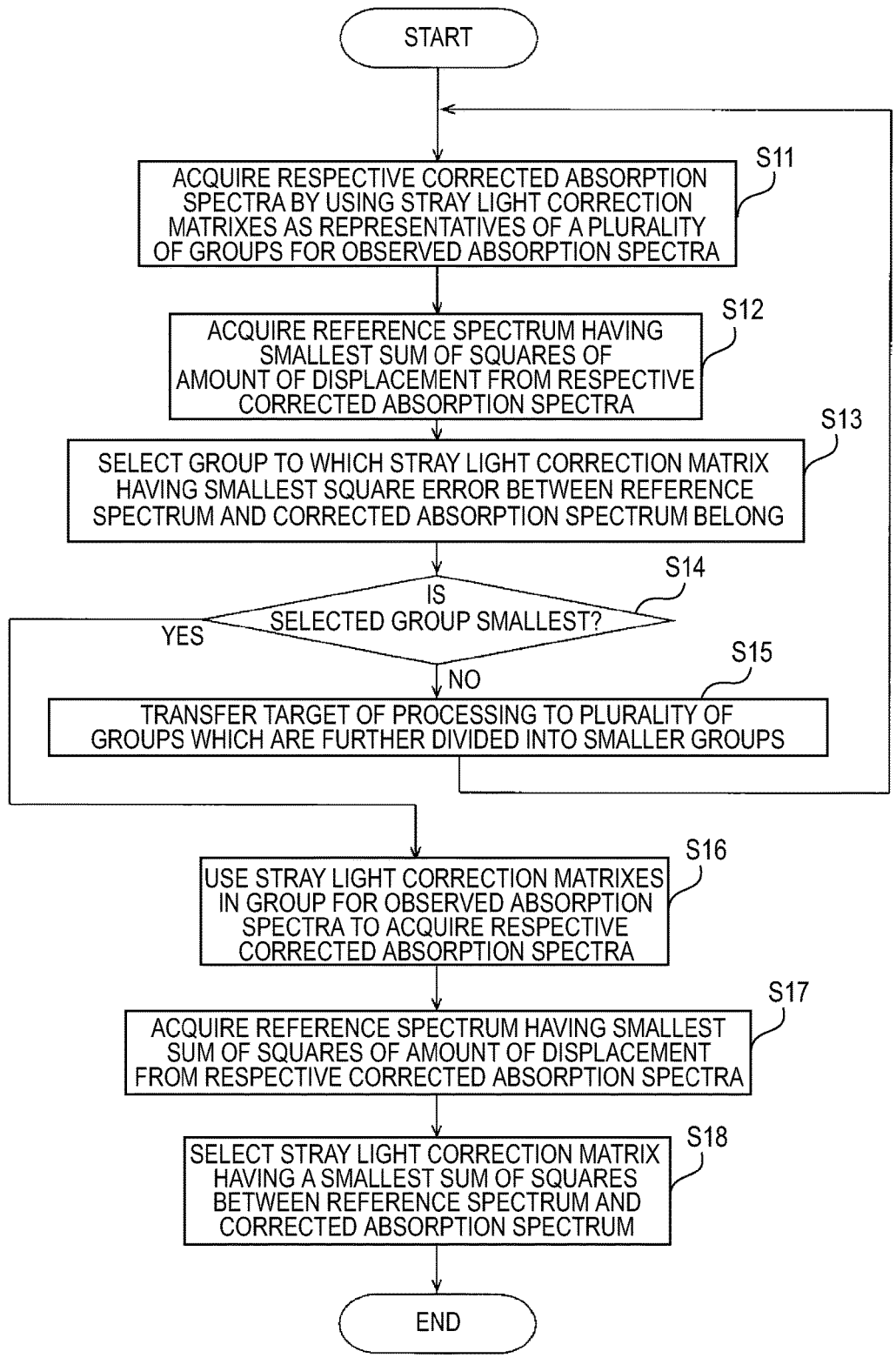
FIG. 6 is a flowchart illustrating a stray light correction matrix selection process according to the embodiment of the invention.

Referring now to FIG. 6, a stray light correction matrix selection process will be described by using a flowchart. The stray light correction matrix selection process is a process of selecting stray light correction matrix $M^{-1}_{(j)}$ adequate for the spectrum analysis apparatus 100 to be calibrated from the stray light correction matrixes $M^{-1}_{(j)}$ based on the measurement with monochromatic light rays and simulation.

When the stray light correction matrix selection process is started, in Step S11, the processing unit 62 acquires a set of a plurality of corrected absorption spectra $Sc_{(j)}$ corresponding to the respective stray light correction matrix $M^{-1}_{(j)}$ by using representative stray light correction matrixes $M^{-1}_{(j)}$ of the respective groups of stray light correction matrixes $M^{-1}_{(j)}$ having similar tendencies for a set of observed absorption spectra So of light transmitted through the plurality of samples S having different light absorption concentrations from each other, and then the procedure goes to Step S12. The group in Step S11 is transferred from the groups divided from the entire stray light correction matrixes $M^{-1}_{(j)}$ to the subgroups in the respective groups, and to the sub subgroups in the respective sub groups, and so forth to the smaller groups every time when Step S11 is repeated.

In Step S12, the processing unit 62 calculates reference spectrum Sr which has a smallest sum of squares of the amount of displacement respectively for each set of the plurality of corrected absorption spectra $Sc_{(j)}$, and then the procedure goes to Step S13.

In Step 13, the processing unit 62 selects a group to which the stray light correction matrix $M^{-1}_{(j)}$ having the smallest square error $\delta_{(j)}$ between the calculated reference spectrum Sr and the corrected absorption spectrum Sc belongs to, and then the procedure goes to Step S14.

In Step S14, the processing unit 62 determines whether or not the selected group is the smallest, and if the selected group is not the smallest (No), the procedure goes to Step S15, and is the selected group is the smallest (Yes), the procedure goes to Step S16. As used herein the term "the smallest group" means that the group in question belongs to the lowest category of classification in the group theory in which the group of stray light correction matrixes $M^{-1}_{(j)}$ is divided into subgroups and then into sub subgroups and so forth in sequence.

In Step S15, the processing unit 62 transfers the target of process to the plurality of groups which are further divided into the stray light correction matrixes $M^{-1}_{(j)}$ having similar tendencies in the selected group of stray light correction matrix $M^{-1}_{(j)}$ and then the procedure returns to Step S11.

In Step S16, the processing unit 62 acquires a set of a plurality of corrected absorption spectra $Sc_{(j)}$ corresponding to the respective stray light correction matrixes $M^{-1}_{(j)}$ by using the plurality of stray light correction matrixes $M^{-1}_{(j)}$ within the smallest group for the set of the observed absorption spectra So, and the procedure goes to Step S17.

In Step S17, the processing unit 62 calculates a reference spectrum Sr which has a smallest sum of squares of the amount of displacement respectively for each set of the plurality of corrected absorption spectra $Sc_{(j)}$, and then the procedure goes to Step S18.

In Step 18, the processing unit 62 selects the stray light correction matrix $M^{-1}_{(j)}$ having the smallest square error $\delta_{(j)}$ between the calculated reference spectrum Sr and the corrected absorption spectrum Sc, and then the stray light correction matrix selection process is ended.

Advantageous Effect of Embodiment

In this embodiment, the following advantageous effects are achieved.

In this embodiment, as described above, the spectrum analysis apparatus 100 is provided with the controller 6 that controls selection of an adequate stray light correction matrix $M^{-1}_{(j)}$ based on a plurality of corrected absorption spectra Sc corrected by stray light correction matrixes $M^{-1}_{(j)}$, which are a plurality of correction devices, acquired in advance for eliminating the effect of stray light, the plurality of corrected absorption spectra So being acquired by using each of a plurality of samples S by correcting a plurality of observed absorption spectra So each indicating absorbance of light passing through samples S, the plurality of samples S having the same light absorbing characteristic with varied degrees of light absorbance and having a peak increased in absorption coefficient for one or plurality of wavelength components. Accordingly, a set of the plurality of corrected absorption spectra Sc is acquired for a set of the plurality of observed absorption spectra So having different degree of light absorbance individually by using the plurality of stray light correction matrixes $M^{-1}_{(j)}$ for the individual stray light correction matrixes $M^{-1}_{(j)}$ and the stray light correction matrixes $M^{-1}_{(j)}$ corresponding to the corrected absorption spectra Sc with the effect of stray light eliminated adequately therefrom are selected from the plurality of corrected absorption spectra Sc. Therefore, correction for eliminating the effect of stray light accurately from the wavelength distribution in a result of measurement is achieved. In other words, adequate stray light correction matrix $M^{-1}_{(j)}$ may be selected based on the same light absorbing characteristic of the plurality of samples S having different amounts of light absorbed therein. Once an adequate stray light correction matrix $M^{-1}_{(j)}$ specific for each instrument of the spectrum analysis apparatus 100 is selected, spectra with the effect of stray light eliminated therefrom may be acquired from then onward only by using the stray light correction matrixes $M^{-1}_{(j)}$ selected for the measured absorption spectra or fluorescent spectra in the measurement of the samples S. In addition, the adequate stray light correction matrix $M^{-1}_{(j)}$ may be selected only by performing measurement by the same number of times as the number of samples S (for example, two to five samples), and calibration may be achieved by using the selected stray light correction matrix $M^{-1}_{(j)}$. Therefore, time required for measurement may be significantly reduced compared with a case where stray light needs to be measured for each of a number of (for example, several hundreds to several thousands of) detection elements included in the detecting unit 51 by using monochromatic light rays. In other words, by selecting an adequate stray light correction matrixes $M^{-1}_{(j)}$ from the plurality of stray light correction matrixes $M^{-1}_{(j)}$ acquired in advance, calibration may be achieved in a short time. Consequently, correction for eliminating the effect of stray light accurately from the wavelength distribution in a result of measurement in a short time is achieved.

In this embodiment, as described above, the controller 6 is configured to align the heights of the peaks of absorbance of the plurality of corrected absorption spectra Sc at peak positions where the absorption coefficient becomes for each of the stray light correction matrixes $M^{-1}_{(j)}$ and based on the deviation of each of the plurality of corrected absorption spectra Sc aligned in height from a reference spectrum Sr, and control the selection of the stray light correction matrixes $M^{-1}_{(j)}$ corresponding to the corrected absorption spectra Sc adequately corrected. Accordingly, based on a nature that the wave shape of the plurality of corrected absorption spectra Sc aligned in height match in an ideal condition having no effect of stray light, the corrected absorption spectra Sc on which the elimination of the effect of stray light has been adequately achieved may be apparent from the margin of degree of deviation from the reference spectrum Sr. Consequently, stray light correction matrixes $M^{-1}_{(j)}$ that correspond to the corrected absorption spectra Sc on which the elimination of the effect of stray light has been adequately achieved and is capable of eliminating the effect of stray light accurately from the wavelength distribution in a result of measurement may be selected. In addition, since the degree of deviation from the reference spectrum Sr is acquired by aligning the height of the plurality of corrected absorption spectra Sc, the height (the peak of absorption) of the corrected absorption spectra Sc before alignment in height may be arbitrary. Accordingly, the heights of the observed absorption spectra So which are the originals of the corrected absorption spectra Sc may also be arbitrary. Therefore, accurate adjustment of the absorption concentrations of the plurality of samples S having the same light absorbing characteristic is not necessary.

In this embodiment, as described above, the controller 6 is configured to control selection of the stray light correction matrixes $M^{-1}_{(j)}$ corresponding to the corrected absorption spectra Sc having deviations within a predetermined range based on the deviation from the reference spectrum Sr, which has a smallest sum of squares of the amount of displacement from the plurality of corrected absorption spectra Sc. Accordingly, the magnitude of the degree of deviation from the reference spectrum may be evaluated accurately, so that whether the elimination of the effect of stray light has been achieved adequately may easily be determined. Consequently, stray light correction matrixes $M^{-1}_{(j)}$ that eliminate the effect of stray light accurately from the wavelength distribution in a result of measurement is selected.

In this embodiment, as described above, the stray light correction matrixes $M^{-1}_{(j)}$ which correspond to the correction devices, are configured to include the stray light correction matrixes $M^{-1}_{(j)}$, which are inverse matrixes of stray light matrixes $M_{(j)}$ acquired in advance and indicating the correspondence relationship between the intensities of the respective wavelength components of light incident on the detector 5 and the intensities of the respective wavelength components as a result of detection. Accordingly, the corrected absorption spectra Sc on which the correction for eliminating the effect of stray light is applied may be acquired from the observed absorption spectra So, which is the result of measurement, immediately by using inverse matrixes of the stray light matrixes $M_{(j)}$. Therefore, the correction for eliminating the effect of stray light accurately from the wavelength distribution in a result of measurement may easily be achieved.

In this embodiment, as described above, the controller 6 is configured to perform calibration based on the plurality of observed absorption spectra So acquired respectively in the samples S obtained by arbitrarily diluting the absorption concentration of the same samples S when performing the calibration based on the plurality of observed absorption spectra So acquired respectively by using the plurality of samples S with varied degrees of light absorbance. Accordingly, calibration may be performed easily based on the plurality of samples S having the same light absorbing characteristic with varied degrees of light absorbance by varying the concentration of the same samples S. In addition, since the degree of dilution of the absorption concentration is arbitrary, accurate measurement is not necessary, and the plurality of samples S may easily be prepared.

In this embodiment, as described above, the controller 6 is configured to perform calibration for eliminating the effect of regularly reflected stray light by a surface portion of the detection elements 52 included in the detector 5 directed to the incident light or the surface portion of the protective member 50 of the detector 5 mounted for protecting the detection elements 52. Accordingly, stray light having a regularity and being caused by regular reflection is also calibrated and thus the plurality of stray light correction matrixes $M^{-1}_{(j)}$ acquired in advance may easily be matched with an ideal stray light correction matrix $M^{-1}_{(j)}$ compared with the case of addressing the effect of irregular stray light generated by diffusion or irregular reflection. Accordingly, by selecting adequate stray light correction matrixes $M^{-1}_{(j)}$ from the plurality of stray light correction matrixes $M^{-1}_{(j)}$ acquired in advance, calibration may be achieved with high degree of accuracy.

In this embodiment, as described above, the controller 6 is configured to perform calibration when mounting at least one of the diffraction grating 4, the detector 5, or the protective member 50 of the detector 5. Accordingly, even when the condition of occurrence of errors caused by regularly reflected stray light when performing maintenance or replacement of the diffraction grating 4, the detector 5 or the protective member 50 of the detector 5, the effect of stray light may be eliminated adequately every time when performing calibration. Accordingly, erroneous measurement caused by stray light which is generated in a different manner by maintenance or replacement may be restrained.

In this embodiment, as described above, the controller 6 is configured to perform calibration based on the plurality of observed absorption spectra So acquired from the samples S having peaks of absorption coefficient in a relatively large wavelength band which is susceptible to a relatively significant effect of the regularly reflected stray light. Accordingly, the effect of stray light on the wavelength components especially around the peaks may be accurately eliminated, and thus the effect of the regularly reflected stray light may be eliminated adequately by using the peaks of the absorption coefficient existing in the relatively large wavelength band which is susceptible to a relatively significant effect of the regularly reflected stray light. Example of Stray light Correction Referring now to FIG. 7 to FIG. 9, a result of calibration using adequate stray light correction matrixes $M^{-1}_{(j)}$ based on comparison between the corrected absorption spectra Sc after calibration including stray light correction considering regular reflection according to this embodiment (example, see FIG. 8) and the corrected absorption spectra Sc after calibration as the state of generation of stray light being uniform irrespective of the positions of the respective detection elements 52 (wavelength components of incident light) (comparative example, see FIG. 9) will be described. The corrected absorption spectra Sc after calibration including stray light correction considering the regular reflection corresponds to the result from which the effect of stray light caused by regular reflection is substantially eliminated because the corrected absorption spectra Sc corresponding to the adequate stray light correction matrixes $M^{-1}_{(j)}$ are selected.

Figure 7:
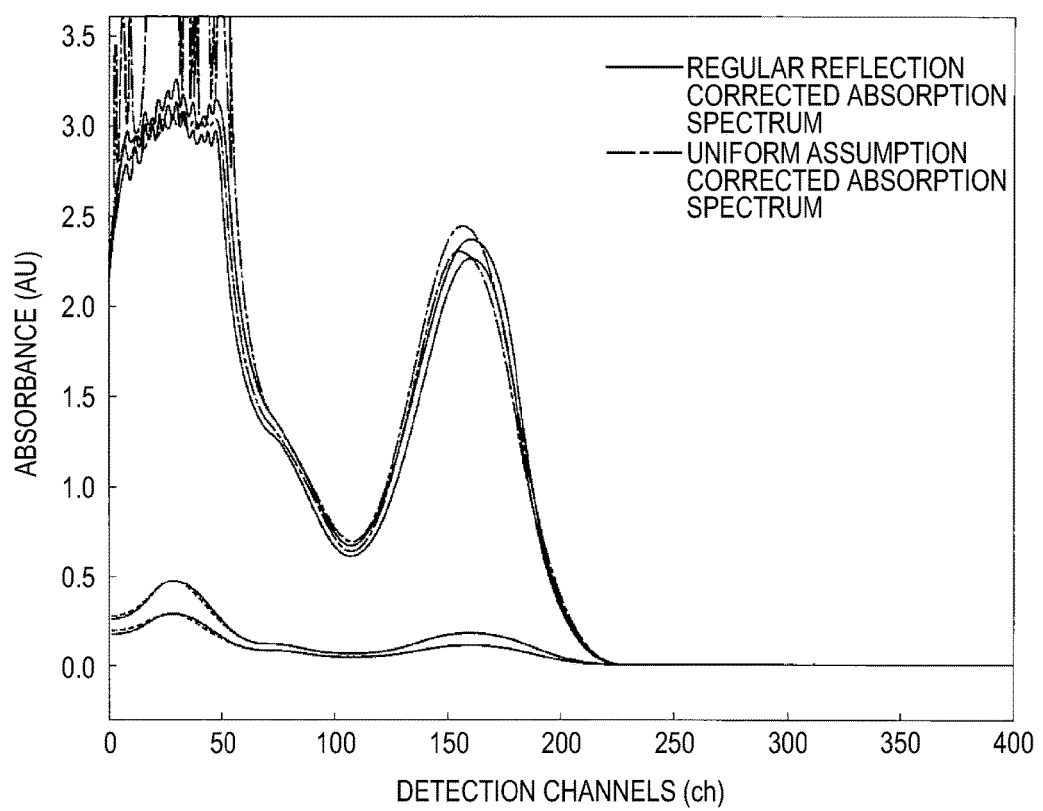
FIG. 7 is a graph illustrating examples of regular reflection corrected absorption spectra and uniform assumption corrected absorption spectra according to the embodiment of the present invention.
Figure 8:
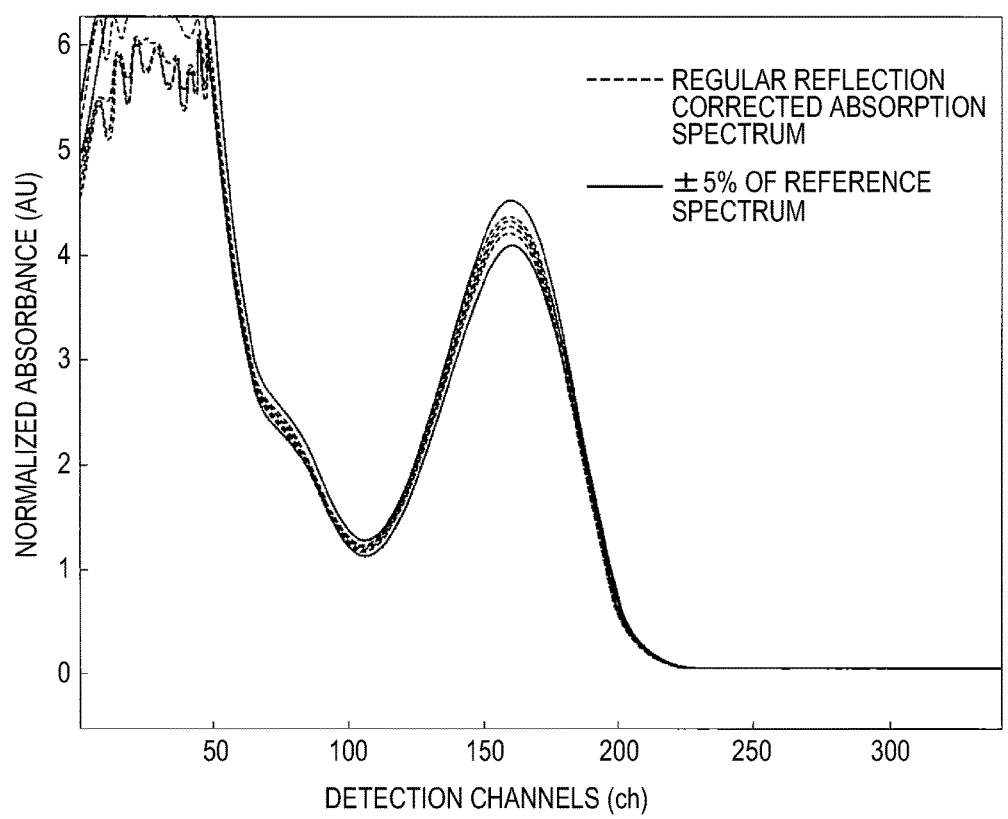
FIG. 8 is a graph illustrating the regular reflection corrected absorption spectra substantially aligned in height according to an example of the embodiment of the invention.

FIG. 7 illustrates a plurality of corrected absorption spectra Sc obtained by correcting a plurality of observed absorption spectra So by using the stray light correction matrixes $M^{-1}$ considering regular reflection (hereinafter, referred to as regular reflection corrected absorption spectrum Sc) and a plurality of corrected absorption spectra Sc obtained by correcting the same observed absorption spectra So under the assumption that generation of stray light is uniform (hereinafter, referred to as uniform assumption corrected absorption spectrum Sc). Here, an adequate stray light correction matrix $M^{-1}$ is already selected from the plurality of stray light correction matrixes $M^{-1}_{(j)}$. The regular reflection corrected absorption spectra Sc are indicated by solid lines in the graph, and the uniform assumption corrected absorption spectra Sc are indicated by dot or dash lines in the graph. The vertical axis indicates the absorbance for each of the wavelength components, and the unit of measurement AU is a read value (arbitrary unit) specific for the instrument. The lateral axis represents the channels (ch) that correspond to respective detection elements 52. The same applies to FIG. 8 and FIG. 9 given below.

In the regular reflection corrected absorption spectra Sc, regular stray light caused by regular reflection is corrected according to the detection elements 52, and other irregular stray light generated uniformly are also corrected. In contrast, in the uniform assumption corrected absorption spectrum Sc, as it is assumed that uniform stray light is generated over the entire detection elements 52, correction in which the effect of stray light different from one detection element 52 to another (from one detected wavelength component to another) is reflected is not performed.

The corrected absorption spectra Sc caused by regular reflection and uniform assumption both include two lines positioned in an upper portion of the graph corresponding to the two samples S having relatively high light absorption concentrations and two lines positioned in a lower portion of the graph corresponding to the two samples S having relatively low light absorption concentrations. Caffeine is used as the sample S. Any of the corrected absorption spectra Sc shows a peak with a high light absorbance near 28 ch and 160 ch that corresponds to the wavelengths at which caffeine exhibits a high absorption coefficient, and shows a peak with a low light absorbance near 60 ch.

Stray light caused by regular reflection in the example illustrated in FIG. 7 is generated by incident light regularly reflected by the surfaces of the detection elements 52 on the long wavelength side being regularly reflected by both surfaces of the protective member 50 and entering again and being detected by the detection elements 52 on the short wavelength side. In other words, unnecessary light is placed on the short wavelength side from the long wavelength side. Consequently, in the observed absorption spectra So, stray light is generated from a side (right side) having a large channel number (ch) which corresponds to the long wavelength to a side (left side) having a small channel number (ch) which corresponds to the short wavelength. As the absorption spectrum represents the magnitude of the light absorbance, if unnecessary light is detected, the spectrum appears to be smaller (lower) correspondingly. Consequently, the peaks of the absorption spectra appear to be relatively lower on the right side due to stray light caused by regular reflection from the side having a large ch number, so that the peaks are deviated to the upper left.

Actually, in FIG. 7, in the two lines of the uniform assumption corrected absorption spectrum Sc having a relatively high absorption concentrations, the peaks near 160 ch are deviated to the upper left when compared with the regular reflection corrected absorption spectra Sc. In this manner, when the effect of the stray light caused by regular reflection appears significantly, the peaks of the absorption spectra are deviated to the upper left as a result. In contrast, in the two lines of the uniform assumption corrected absorption spectrum Sc having a relatively low absorption concentrations, the peaks near 160 ch are not much deviated when compared with the regular reflection corrected absorption spectra Sc. Such a difference is caused by the fact that when the absorption concentration is high, light transmitted through the sample S includes little wavelength component that corresponds to the peak of the absorption coefficient and, on the other hand, when the absorption concentration is low, light transmitted through the sample S relatively includes the wavelength component that corresponds to the peak of the absorption coefficient remained therein. In the case where light transmitted through the sample S includes little wavelength component that corresponds to the peak of the absorption coefficient, the resulted peak of the absorbance changes significantly even with a little amount of stray light detected by the detection elements 52 that detect the corresponding wavelength components. In contrast, in the case where light transmitted through the sample S includes the wavelength components that correspond to the peak of the absorption coefficient to some extent, the effect of stray light is relatively reduced, and hence the effect of stray light does not appear that much. From these results, it is understood that the effect of the stray light appears significantly especially for the wavelength components having high light absorbance.

The two lines of the uniform assumption corrected absorption spectra Sc having relatively high absorption concentrations have acutely wavy shaped peaks near 28 ch. It is because the light absorbance of the sample S is high and thus the wavelength component corresponding to near 28 ch is reduced the transmitted light to a value near zero, and consequently the effect of stray light caused by regular reflection appears significantly and directly. Also the two lines of the regular reflection corrected absorption spectra Sc having relatively high absorption concentration shows the effect of stray light caused by regular reflection remaining near 28 ch to some extent. The two lines of regular reflection and uniform assumption corrected absorption spectra Sc having relatively low absorption concentration do not show waving due to stray light caused by regular reflection. However, the shape of the peaks of the uniform assumption corrected absorption spectra Sc are slightly deviated to the upper left with respect to the shape of the peaks of the regular reflection corrected absorption spectra Sc.

FIG. 8 is a graph (Example) in which the heights of the regular reflection corrected absorption spectra Sc are aligned. The respective dot lines indicate the regular reflection corrected absorption spectra Sc corresponding to the samples S having different concentrations. Two lines indicated by solid lines show the width of ±5% with respect to the reference spectrum Sr which is set to have the minimum square error with respect to the regular reflection corrected absorption spectra Sc. As the absorbance is defined by the logarithm, the width of ±5% is increased with an increase in value of the absorbance in appearance. The regular reflection corrected absorption spectrum Sc illustrated in FIG. 8 is a result of utilization of the most adequate stray light correction matrix $M^{-1}$ out of the results of utilization of a number of the stray light correction matrixes $M^{-1}$ for the observed absorption spectra So. Therefore, as apparent from FIG. 8, all the regular reflection corrected absorption spectra Sc substantially match except for a portion where waving occurred due to stray light, and are within a width of ±5% with respect to the reference spectrum Sr. The value of ±5% is an example only.

FIG. 9 illustrates a graph (comparative example) showing the uniform assumption corrected absorption spectra Sc applied with the process of aligning the height as the process applied to the regular reflection corrected absorption spectra. Respective graphs indicated by dot lines are graphs of the uniform assumption corrected absorption spectra Sc corresponding to the samples S having different concentrations. The two solid lines in the graph indicate a width of ±5% with respect to the reference spectrum Sr calculated from the regular reflection corrected absorption spectra, and the same as those in FIG. 8. As apparent from FIG. 9, since the effect of stray light caused by regular reflection is not adequately eliminated, the lines of the uniform assumption corrected absorption spectra Sc do not match. It shows that the peaks of the uniform assumption corrected absorption spectra Scare deviated to the upper left near 160 ch.

In comparison between Example and Comparative Example, it is clear that stray light containing stray light different from one detection element 52 to another caused by regular reflection is adequately eliminated in Example. Therefore, it is understood that adequate calibration is achieved by the calibration method that selects the stray light correction matrixes $M^{-1}_{(j)}$ capable of eliminating stray light adequately as in Example.

The spectrum analysis apparatus 100 subjected to calibration is capable of acquiring spectra having the effect of stray light eliminated adequately by using adequately selected stray light correction matrixes $M^{-1}_{(j)}$ that are correction devices for the absorption spectra, fluorescent spectra, and the like of substances to be measure from then onward.

Modification

The embodiment and Example disclosed here are to be considered as examples only in all respects and are not intended to limit the invention. The scope of the invention is not the description of the embodiment and example given above, and is defined by claims, and includes any alteration (modifications) within a scope of claims and within a meaning and a scope equivalent to claims.

For example, in the embodiment described above, an example in which caffeine is used as the sample S for performing calibration. However, the invention is not limited hereto. In the invention, the sample S may be a naphthalene or phenols. The naphthalene, having the plurality of peaks of light absorption on the short wavelength side, is suitable for calibration on the short wavelength side. Caffeine and phenols, having peaks of light absorption on the long wavelength side compared with naphthalene, are suitable for calibration on the relatively long wavelength side. For example, by using the sample S of a mixture of naphthalene and caffeine, peaks on both the short wavelength side and the long wavelength side are obtained. Stray light generated by geometric tolerance of the mounting angle of the protective member 50 with respect to the detecting unit 51 varies proportionally to the relative deviation of the detecting positions, and thus calibration with higher degree of accuracy is achieved by measuring two points apart from each other on the short wavelength side and the long wavelength side. Therefore, calibration with higher degree of accuracy is achieved by using a sample S having peaks both on the short wavelength side and the long wavelength side.

The spectrum analysis apparatus 100 in the states of generation of stray light caused by regular reflection, which are different from one instrument to another of the spectrum analysis apparatus 100, varies depending on the difference in mounting angle between the protective member 50 and the detecting unit 51 in FIG. 3, the difference in stray light appearance distance from one instrument to another caused by difference in thickness of the silicon layer 511 included in the detecting unit 51, upward and downward shifting of the entire graph, or difference in leftward and rightward shift of the wave shapes of the graph from one instrument to another in FIG. 4, and thus, theoretically, vary depending mainly on four parameters. Therefore, the sample S for performing calibration allows selection of stray light correction matrixes $M^{-1}_{(j)}$ with high degree of accuracy as long as it includes four or more peaks of light absorption. However, when selecting the stray light correction matrixes $M^{-1}_{(j)}$ determination does not made only from one point at the peaks, but also from coincidence of the entire graph of the corrected absorption spectra Sc aligned in height. Therefore, the stray light correction matrixes $M^{-1}_{(j)}$ may be selected with high degree of accuracy even when there is only one peak point.

If the aforesaid peaks of light absorption at four or more points exist within a wide range of wavelength (the wavelength detected by the detector 5) to be calibrated with the wavelength components exhibiting a wide angle of regular reflection, it is preferable because calibration with higher degree of accuracy is achieved. For example, if the sample S is a mixture of naphthalene, caffeine, and phenols described above, conditions may satisfies conditions described thus far in the example of the spectrum analysis apparatus 100 that detects the wavelength components from 190 nm to 800 nm in the embodiment. Note that measurement is performed at more or less five points for evaluation of linearity of a detected signal at the time of calibration, and hence calibration for stray light and evaluation of linearity may be performed simultaneously.

Although the aforesaid embodiment describes an example in which the liquid chromatograph 101 is connected to the spectrum analysis apparatus 100, the invention is not limited thereto. According to the invention, a gas chromatograph or a mass analysis apparatus may be connected to the spectrum analysis apparatus 100. In addition, the spectrum analysis apparatus 100 may be used widely in various application for measuring light spectra such as measurement of light absorbance spectra that transmit through chemicals in the course of manufacture to observe phases of production of chemicals. Furthermore, the controller 6 for calibration of the invention may be provided in various types of spectrum analysis apparatus 100 such as a spectrum analysis apparatus 100 configured to measure absorption spectra by making white light transmit through substances, a spectrum analysis apparatus 100 configured to measure absorption spectra by making UV rays transmit through substances or to measure fluorescence released from substances.

Although the aforesaid embodiment describes an example in which the sample S to be measured when performing calibration on the spectrum analysis apparatus 100 is a sample S of a form flowing in the liquid chromatograph 101, the invention is not limited thereto. In the invention, for example, the stray light correction matrixes $M^{-1}_{(j)}$ may be selected by replacing a plurality of samples S having the same light absorbing characteristic, being different in concentration from each other and being encapsulated in a sealing cell at the position of the flow cell 75 of the liquid chromatograph 101 in sequence and measuring the respective observed absorption spectra So. Alternatively, the plurality of samples S different in absorption concentration from each other may be used by combining a plurality of optical filters having the same light absorbing characteristic. In this case, the absorption concentration of the sample S may be adjusted by changing a light transmitting distance with respect to the sample S by increasing or reducing the number of the optical filters placed on a light route incident on the diffraction grating 4 or the absorption concentration of the sample S may be adjusted by changing a light transmission distance with respect to the sample S by changing the combination of the optical filters having different thicknesses to measure the plurality of observed absorption spectra So.

Although the aforesaid embodiment describes an example in which the stray light correction matrixes $M^{-1}_{(j)}$ are used as the correction devices, the present invention is not limited thereto. In the invention, the stray light correction matrixes $M^{-1}_{(j)}$ do not have to be used as the correction devices. In this case, for example, the correction devices may be configured to subtract estimated stray light by wavelength components of the observed absorption spectra So.

Although the aforesaid embodiment describes an example in which the correction devices are directed mainly to stray light, the invention is not limited thereto. In the invention, correction devices that cover fluctuations in measurement value due to noise caused by a dark current of the instruments or changes in temperature of the instruments in addition to stray light and are capable of performing calibration that can widely eliminate measurement error.

Although the aforesaid embodiment describes an example in which calibration is performed by using the plurality of samples S such as caffeine having the same light absorbing characteristic with different absorption concentrations but having arbitrary concentrations under assumption that contamination or the like may occur in the samples S, the invention is not limited thereto. In the invention, the concentration of the sample S may be adjusted completely to a predetermined concentration and calibration may be performed by using a plurality of known samples S which have no contamination in substances contained in the samples S. In this case, a number of known observed absorption spectra $So_{(k)}$ acquired in advance and the observed absorption spectra So acquired by measurement are compared to select adequate stray light correction matrix $M^{-1}_{(k)}$. Here, reference sign k represents numbers corresponding to a plurality of instruments and simulations of the spectrum analysis apparatus 100. Specifically, sets of observed absorption spectra $So_{(k)}$ obtained as a result of usage of a plurality of known samples S with respect to the plurality of spectrum analysis apparatus 100 in advance are acquired, and stray light correction matrixes $M^{-1}_{(k)}$ that are capable of eliminating the effect of stray light in advance corresponding to the respective sets of observed absorption spectra $So_{(k)}$ are acquired, and these sets are stored in the memory unit 61. In addition, sets of the observed absorption spectra $So_{(k)}$ and the stray light correction matrixes $M^{-1}_{(k)}$ estimated within a range of geometric tolerance and stray light correction matrixes $M^{-1}_{(k)}$ are prepared from the sets of the observed absorption spectra Soak) and the stray light correction matrix $M^{-1}_{(k)}$ for interpolation and are also stored in the memory unit 61. Accordingly, the processing unit 62 is allowed to perform calibration adequately by calculating the square error and evaluating the degree of matching between the sets of the observed absorption spectra So acquired by measurement and the known observed absorption spectra $So_{(k)}$ acquired in advance.

In this case, the state of generation of stray light corresponding to the set of the observed absorption spectra $So_{(k)}$ having the highest degree of matching and the state of generation of stray light of the spectrum analysis apparatus 100 to be calibrated seem to be substantially the same. Therefore, the processing unit 62 is capable of performing calibration by selecting the stray light correction matrixes $M^{-1}{}_{(k)}$ corresponding to the set of the observed absorption spectra $So_{(k)}$ having the highest degree of matching.

Although the aforesaid embodiment describes an example in which interpolative stray light matrixes $M_{(j)}$ may be created theoretically by simulation by listing the state of generation of stray light that may exist within a range of geometric tolerance, the invention is not limited thereto. In the invention, the stray light correction matrixes $M^{-1}{}_{(j)}$, which are a plurality of inverse matrixes that introduce an output light from the detected light by using the state of generation of various instruments measured directly by monochromatic light rays incident normally on the positions of the detection elements 52 may be created from the empirical rule. In this case as well, the controller 6 selects stray light correction matrixes $M^{-1}{}_{(j)}$ which can bring the corrected absorption spectra Sc aligned adequately in height to match each other as correction devices adequate for calibration.

Although the aforesaid embodiment describes an example in which adequate stray light correction matrixes $M^{-1}{}_{(j)}$ are selected by repeating processing of the representative stray light correction matrixes $M^{-1}{}_{(j)}$ in the stray light correction matrixes $M^{-1}{}_{(j)}$ grouped so as to be branched from large groups to small groups as a tree diagram in a round robin method, the invention is not limited thereto. In the invention, differential amounts and varying amounts relative to components of the matrix may be acquired between the plurality of stray light correction matrixes $M^{-1}{}_{(j)}$ to select adequate stray light correction matrixes $M^{-1}{}_{(j)}$ by another algorithm such as the gradient method or Newton's method. Searching adequate stray light correction matrixes $M^{-1}{}_{(j)}$ may be started from randomly picked up stray light correction matrixes $M^{-1}{}_{(j)}$ instead of the representative stray light correction matrixes $M^{-1}{}_{(j)}$. In addition, an algorithm of a combination of the above-descried methods is also applicable. Processing may be configured to be performed on all the stray light correction matrixes $M^{-1}{}_{(j)}$ in a round robin method.

Although the aforesaid embodiment describes an example in which the degree of matching of the corrected absorption spectra $Sc_{(j)}$ aligned in height is directed to matching of the corrected absorption spectra $Sc_{(j)}$ aligned in height as a whole, the invention is not limited thereto. In the invention, acquirement of the degree of matching of the corrected absorption spectra $Sc_{(j)}$ aligned in height may be directed only at the peak portions or the peripheries of the peak portions of the corrected absorption spectra $Sc_{(j)}$.

Although the aforesaid embodiment describes an example in which stray light correction matrixes $M^{-1}{}_{(j)}$ having the smallest sum of squares of the amount of displacement with respect to a reference spectrum which corresponds to the one that matches most with corrected absorption spectra $Sc_{(j)}$ aligned in height out of sets of the corrected absorption spectra $Sc_{(j)}$, the invention is not limited thereto. In the invention, the plurality of corrected absorption spectra $Sc_{(j)}$ that fall within an allowable range may be selected, and the stray light correction matrix $M^{-1}{}_{(j)}$ having the highest degrees of correlation with the original observed absorption spectra So may be selected from the selected plurality of corrected absorption spectra $Sc_{(j)}$. Here, the stray light correction matrixes $M^{-1}{}_{(j)}$ that falls within the allowable range are, for example, the stray light correction matrixes $M^{-1}{}_{(j)}$ corresponding to those with which all the corrected absorption spectra $Sc_{(j)}$ aligned in height falls within a predetermined allowable range such as a range ±5% in FIG. 8. The stray light correction matrixes $M^{-1}{}_{(j)}$ having the highest degree of correlation between the corrected absorption spectra $Sc_{(j)}$ and the original observed absorption spectra So may be, for example, the stray light correction matrixes $M^{-1}{}_{(j)}$ corresponding to the corrected absorption spectrum $Sc_{(j)}$ having the smallest square error between the observed light amount of the corrected absorption spectra Sc and the observed light amount of the original observed absorption spectra So.

In the case where the absorption concentration of the sample S is high, the portion of the corrected absorption spectra $Sc_{(j)}$ having high absorbance may become a value close to zero at spectra that indicate light intensities before being corrected to the spectra of absorbance because little light is observed. At this time, when the stray light correction matrixes $M^{-1}{}_{(j)}$ is applied to the observed absorption spectra So, negative values may be generated by correction at spectra which indicate intensity and consequently, waving as illustrated near 28 ch in FIG. 7 appears in the corrected absorption spectra $Sc_{(j)}$. As a result, the graph becomes difficult to read, and determination of degree of matching becomes difficult. Therefore, in addition to the evaluation of the square error of the amount of displacement between the corrected absorption spectrum $Sc_{(j)}$ and the reference spectrum Sr, a penalty (negative evaluation) may be added when a negative value is generated in the spectra that indicate intensity. Consequently, adequate stray light correction matrix $M^{-1}{}_{(j)}$ may be selected among the correction matrixes $M^{-1}{}_{(j)}$ which are slightly lack of correction and do not generate a negative value except for the stray light correction matrixes $M^{-1}{}_{(j)}$ which may apply excessive correction and generate a negative value.

Although the aforesaid embodiment describes the stray light correction matrix preparation process and the stray light correction matrix selection process by the processing unit 62 included in the controller 6 by using a flowchart of "flow driving type" for the sake of convenience, the present invention is not limited thereto. The process of the processing unit 62 may be performed by an "event driving type" that is executed by the unit of event. In this case, the process may be performed by the complete event driving type and may be performed with a combination of the event driving type and the flow driving type.

What is claimed is:

1. A spectrum analysis apparatus comprising:
   a spectral member configured to split light incident thereon by wavelength components;
   a detector configured to measure intensities of light rays split by the wavelength components by means of the spectral member; and
   a controller configured to perform calibration including a correction for eliminating an effect of stray light incident on the detector, which is light not to be measured, wherein
   the controller controls selection of an adequate correction device based on a plurality of corrected absorption spectra corrected by a plurality of the correction devices acquired in advance for eliminating the effect of stray light, the plurality of corrected absorption spectra being acquired by correcting a plurality of observed absorption spectra each indicating absorbance of light passing through a plurality of samples, the plurality of samples having the same light absorbing characteristic with varied degrees of light absorbance and having a peak increased in absorption coefficient for one or a plurality of wavelength components.

2. The spectrum analysis apparatus according to claim 1, wherein
the controller aligns heights of peaks of absorbance of a plurality of the corrected absorption spectra at peak positions where the absorption coefficients become high for each of the correction devices, and based on deviation of each of the plurality of corrected absorption spectra aligned in height from a reference spectrum, controls to select a correction device corresponding to the corrected absorption spectrum adequately corrected.

3. The spectrum analysis apparatus according to claim 2, wherein
the controller controls selection of the correction device corresponding to the corrected absorption spectrum having deviations within a predetermined range based on the deviation from the reference spectrum, which has a smallest sum of squares of an amount of displacement from the plurality of corrected absorption spectra.

4. The spectrum analysis apparatus according to claim 1, wherein
the correction device includes a stray light correction matrix, which is an inverse matrix of stray light matrix acquired in advance and indicating a correspondence relationship between the intensities of respective wavelength components of light incident on the detector and intensities appeared on the respective wavelength components as a result of detection.

5. The spectrum analysis apparatus according to claim 1, wherein
when the controller performs the calibration based on the plurality of observed absorption spectra acquired respectively by using the plurality of samples with varied degrees of light absorbance, the controller performs calibration based on the plurality of observed absorption spectra acquired respectively in the plurality of samples obtained by arbitrarily diluting the absorption concentration of the same samples.

6. The spectrum analysis apparatus according to claim 1, wherein
the controller performs calibration for eliminating the effect of stray light regularly reflected by surface portions of the detection elements included in the detector and directed to the incident light or by a surface portion of a protective member of the detector mounted for protecting the detection elements.

7. The spectrum analysis apparatus according to claim 6, wherein
the controller performs calibration when mounting at least one of the spectral member, the detector, and the protective member of the detector.

8. The spectrum analysis apparatus according to claim 6, wherein
the controller performs calibration based on the plurality of observed absorption spectra acquired from the sample having a peak of absorption coefficient in a relatively large wavelength band which is susceptible to a relatively significant effect of regularly reflected stray light.

9. A calibration method including correction for eliminating an effect of stray light by a spectrum analysis apparatus including a spectral member configured to split light incident thereon by wavelength components and a detector configured to measure intensities of light rays split by the wavelength components by means of the spectral member, comprising:
acquiring a plurality of observed absorption spectra each indicating absorbance of light passing through a plurality of samples by using each of the plurality of samples having the same light absorbing characteristic with varied degrees of light absorbance and having a peak increased in absorption coefficient for one or plurality of wavelength components, and selecting an adequate correction device based on a plurality of corrected absorption spectra corrected by a plurality of the correction devices acquired in advance for eliminating the effect of stray light.

* * * * *